(12) United States Patent
Bruestle

(10) Patent No.: US 7,968,337 B2
(45) Date of Patent: Jun. 28, 2011

(54) NEURAL PRECURSOR CELLS, METHOD FOR THE PRODUCTION AND USE THEREOF IN NEURAL DEFECT THERAPY

(76) Inventor: Oliver Bruestle, Meckenheim (DE)

(*) Notice: Subject to any disclaimer, the term of this patent is extended or adjusted under 35 U.S.C. 154(b) by 310 days.

(21) Appl. No.: 12/048,840

(22) Filed: Mar. 14, 2008

(65) Prior Publication Data

US 2008/0213888 A1 Sep. 4, 2008

Related U.S. Application Data

(62) Division of application No. 09/581,890, filed as application No. PCT/DE98/03817 on Dec. 18, 1998, now abandoned.

(30) Foreign Application Priority Data

Dec. 19, 1997 (DE) .................................. 197 56 864

(51) Int. Cl.
| | |
|---|---|
| C12N 5/00 | (2006.01) |
| C12N 5/02 | (2006.01) |
| C12N 5/071 | (2010.01) |
| C12N 5/07 | (2010.01) |
| C12N 5/10 | (2006.01) |

(52) U.S. Cl. ........ 435/377; 435/375; 435/325; 435/354; 435/366; 435/368

(58) Field of Classification Search ........................ None
See application file for complete search history.

(56) References Cited

U.S. PATENT DOCUMENTS

5,980,885 A * 11/1999 Weiss et al. ................ 424/93.21
2007/0009491 A1 * 1/2007 Weiss et al. .................. 424/93.7

FOREIGN PATENT DOCUMENTS

DE 19756864.5 12/1997

OTHER PUBLICATIONS

Bjorklund, in: Molecular and Cellular Approaches to the Treatment of Neurological Disease, Raven Press, New York, 1993.
Brustle & McKay, Curr. Opinion Neurobiol. 6:688-695, (1996).
Lindvall, in: Neural transplantation in Parkinson's disease, Raven Press, New York, 1994.
Olanow et al., TINS 19:102-109, (1996).
Lendahl & McKay, TINS 13:132-173, (1990).
Renfranz et al., Cell 66:713-729, (1991).
Westerman & Leboulch, Proc. Natl. Acad. Sci. USA 93:8971-8976, (1996).
Cattaneo & McKay, Nature 347:762-765, (1990).
Reynolds & Weiss, Science 255:1707-1710, (1992).
Richards et al., Proc. Natl. Acad. Sci. USA 89:8591-8595, (1992).
Ray et al., Proc. Natl. Acad. Sci. USA 90:3602-3606, (1993).
Kilpatrick & Bartlett, Neuron 10:255-265, (1993).
Ray & Gage, J. Neurosci. 6:3548-3564, (1994).
Davis & Temple, Nature 372:263-266, (1994).
Vicario-Abejon et al., Neuron 15:105-114, (1995).
Gosh & Greenberg, Neuron 15:89-103, (1995).
Gritti et al., J. Neurosci. 16:1091-1100, (1996).
Svendsen et al., Exp. Neurol. 137: 376-388, (1996).
Gage et al., Proc. Natl. Acad. Sci. USA 92:11879-11883, (1995).
Martin, Proc. Natl. Acad. Sci. USA 78:7634-7638, (1981).
Evans & Kaufman, Nature 292:154-156, (1981).
Bradley et al., Nature 309:255-256, (1984).
Smith et al., Nature 336:688-690, (1988).
Robertson et al., Nature 323:445-448, (1986).
Iannaconne et al., Dev. Biol. 163:288-292, (1994).
Doetschman et al., Dev. Biol. 127:224-227, (1988).
Pain et al., Development 122:2339-2348, (1996).
Sun et al., Mol. Mar. Biol. Biotechno. 4:193-199, (1995).
Wheeler, Reprod. Fertil. Dev. 6:563-568, (1994).
First et al., Reprod. Fertil. Dev. 6:553-562, (1994).
Thomson et al., Science 282:1145-1147, (1998).
Shamblott et al., Proc. Natl. Acad. Sci. USA 95:13726-13731, (1998).
Campbell et al., Nature 380:64-66, (1996).
Wilmut et al., Nature 385:810-813, (1997).
Bain et al. Dev. Biol. 168:342-357, (1995).
Strubing et al., Mech. Dev. 53:275-287, (1995).
Fraichard et al., J. Cell Sci. 108:3181-3188, (1995).
Finley et al., J. Neurosci. 16:1056-1065, (1996).
Frederiksen & McKay, J. Neurosci. 8:1144-1151, (1988).
Lendahl et al., Cell 60:585-595, (1990).
Okabe, in: Current Protocols in Neuroscience, John Wiley, New York, 1997.
Dinsmore et al., Cell Transplant 5:131-143, (1996).
Nagy et al., Proc. Natl. Acad. Sci. USA 90:8424-8428, (1993).
Swiatek & Gridley, Genes Dev. 7:2071-2084, (1993).
Thomson et al. Proc. Natl. Acad. Sci. USA 92:7844-7848, (1995).
Ericson et al., Cell 81:747-756, (1995).
Wang et al., Nature Med. 1:1184-1188, (1995).
Eisenbarth et al., Proc. Natl. Acad. Sci. USA 76:4913-4917, (1979).
Bjorklund et al., in: Functional Neural Transplantation, Seiten 157-195, Raven Press, New York, (1994).

* cited by examiner

*Primary Examiner* — Anne-Marie Falk
(74) *Attorney, Agent, or Firm* — Barnes & Thornburg LLP; Alice O. Martin

(57) ABSTRACT

The invention relates to isolated and purified neural precursor cells, to methods for the generation of such precursor cells in unlimited quantities from embryonic stem cells, and to their use for the therapy of neural defects, particularly in mammals, preferably in human beings, and for the generation of polypeptides.

16 Claims, 8 Drawing Sheets

Fig.4A
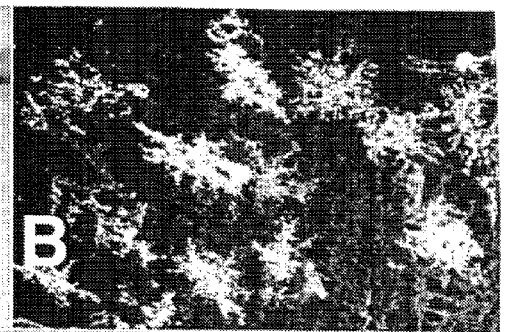
4B
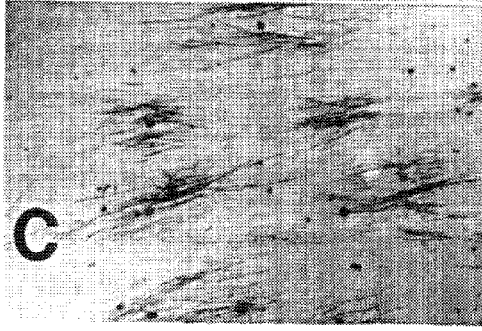
Fig.4C
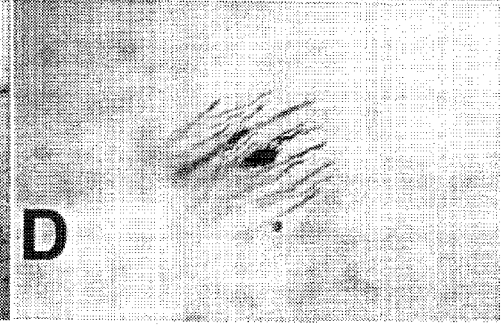
4D

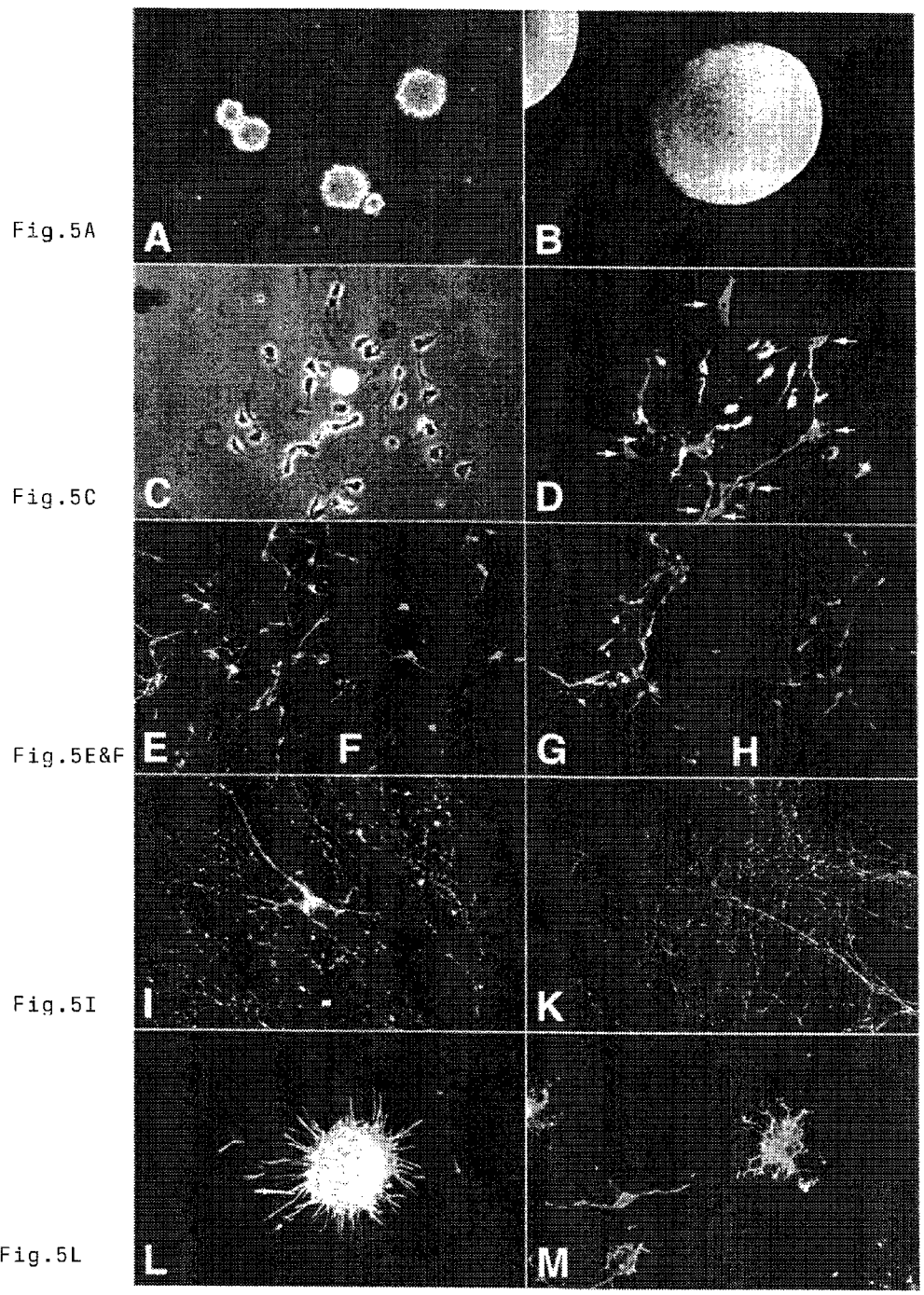

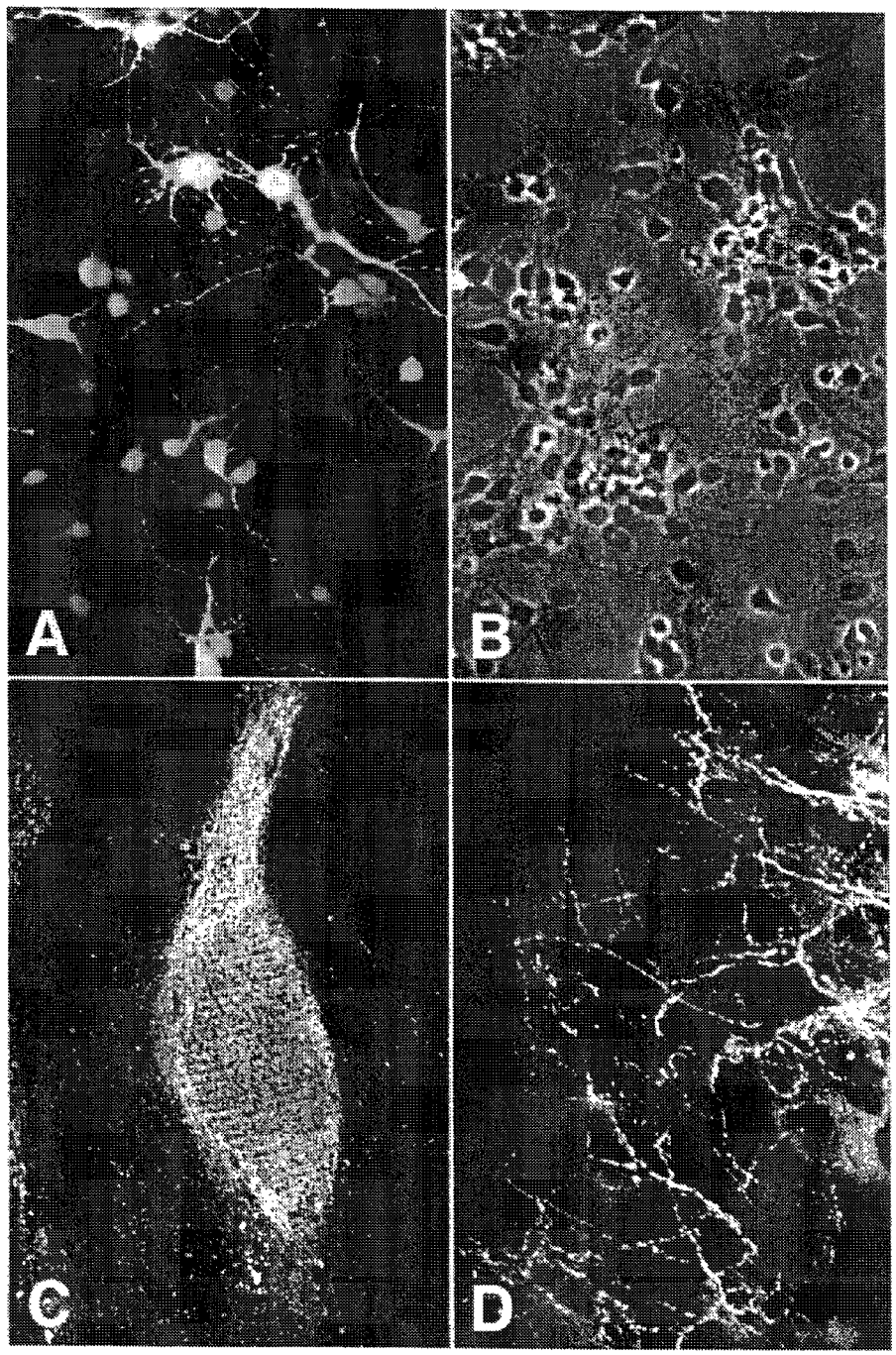

NEURAL PRECURSOR CELLS, METHOD FOR THE PRODUCTION AND USE THEREOF IN NEURAL DEFECT THERAPY

CROSS REFERENCE TO RELATED APPLICATIONS

This application is a Divisional of U.S. application Ser. No. 09/581,890, filed Aug. 28, 2000 now abandoned, which is a U.S. nationalization of international application no. PCT/DE98/03817, filed Dec. 18, 1998, which claims priority to German application no. DE19756864.5, filed Dec. 19, 1997.

The invention relates to isolated and purified embryonic stem cell-derived neural precursor cells, to methods for the generation of such precursor cells in unlimited quantities, and to their use for I) the therapy of neural defects, particularly in mammals, preferably in human beings, and II) for the generation of polypeptides.

Transplantation of neural cells into the nervous systems of mammals represents a promising method for the treatment of numerous neurological diseases. In animal studies, a variety of cell populations have been grafted into the brain and spinal cord (Björklund, in: Molecular and Cellular Approaches to the Treatment of Neurological Disease, Raven Press, New York, 1993; Brüstle & McKay, Curr. Opinion Neurobiol. 6:688-695, 1996). Recently, neural transplantation has also been applied for the clinical treatment of selected diseases, for example for the treatment of patients with Parkinsons disease (Lindvall, in: Neural transplantation in Parkinson's disease, Raven Press, New York, 1994; Olanow et al., TINS 19:102-109, 1996).

In contrast to many other organs, the mature mammalian nervous system shows only a very limited regeneration potential. This is due to the fact that precursor cells required for generating neural tissue are, with few exceptions, restricted to nervous system development. The availability of precursor cells is a key prerequisite for a transplant-based repair of defects in the mature nervous system. Thus, donor cells for neural transplants are largely derived from the embryonic brain. For example, brain tissue from up to seven human embryos is required to obtain a sufficient amount of donor tissue for the transplantation of an individual Parkinson patient. This creates enormous ethical problems, and it is questionable whether such an approach can be used for the treatment of a large number patients.

Recently there have been numerous efforts to bypass the limited availability of mammalian embryonic brain cells by in vitro proliferation of precursor cells prior to transplantation. Two major strategies were used. One method comprises the immortalization of precursor cells with oncogenes. Most of the genes used for this approach have been originally isolated from tumor tissue. These "tumor genes" are inserted into the genome of the cells and elicit continuous and ill-controlled growth (Lendahl & McKay, TINS 13:132-137, 1990).

More recent and better controlled variants of this technique employ temperature-sensitive oncogenes. This approach permits the in vitro proliferation of the cells under the "permissive" temperature. The non-permissive temperature is chosen to equal the body temperature, resulting in instability of the gene product and ceasing of proliferation after transplantation (Renfranz et al., Cell 66:713-729, 1991). However, the oncogen remains in the transplanted cells, and low activity or reactivation at a later time point cannot be entirely excluded. Newer strategies have been aiming at the removal of the oncogene after completion of the proliferation phase, using molecular biological tools (Westerman & Leboulch, Proc. Natl. Acad. Sci. USA 93:8971-8976, 1996). As all cell lines, oncogen-immortalized precursor cells exhibit a high susceptibility to chromosomal aberrations.

Another method for the in vitro proliferation of precursor cells prior to transplantation is the stimulation of proliferation with growth factors (Cattaneo & McKay, Nature 347:762-765, 1990; Reynolds & Weiss, Science 255:1707-1710, 1992; Richards et al., Proc. Natl. Acad. Sci. USA 89:8591-8595, 1992; Ray et al., Proc. Natl. Acad. Sci. USA 90:3602-3606, 1993; Kilpatrick & Bartlett, Neuron 10:255-265, 1993; Ray & Gage, J. Neurosci. 6:3548-3564, 1994; Davis & Temple, Nature 372:263-266, 1994; Vicario-Abejon et al., Neuron 15:105-114, 1995; Gosh & Greenberg, Neuron 15:89-103, 1995; Gritti et al., J. Neurosci. 16:1091-1100, 1996). It is currently unclear to what extent growth factors permit an in vitro expansion of neural precursors. First transplant studies using growth factor-treated cells show controversial results. Whereas some scientists observed a decreased ability of these cells to integrate into the host tissue (Svendsen et al., Exp. Neurol. 137:376-388, 1996), there are studies that suggest that growth factor-treated cells can incorporate into the recipient brain (Gage et al., Proc. Natl. Acad. Sci. USA 92:11879-11883, 1995).

In summary, the order of magnitude of growth factor-mediated neural precursor cell proliferation and the biological behavior of these proliferated cells following transplantation into a host nervous system are currently unclear. Oncogene-mediated cell expansion strategies carry a high risk with respect to chromosomal aberrations and potential tumor induction. The most severe disadvantage of these strategies is the fact that they both depend on the availability of brain tissue, mostly derived from embryonic donors.

Embryonic stem cells (ES cells) provide entirely new perspectives for the generation of donor cells for transplantation. ES cells were first described in mice in 1981 (Martin, Proc. Natl. Acad. Sci. USA 78:7634-7638, 1981; Evans & Kaufman, Nature 292:154-156, 1981). They can be derived, for example, from the inner cell mass of 3, 5-day-old embryos. ES cells are pluripotent and can generate all tissues and cell types. This is best reflected by the fact that ES cells injected into another blastocyst can participate in the generation of all tissues including the germ line, thereby yielding chimeric animals (Bradley et al., Nature 309:255-256, 1984). A unique feature of ES cells is the fact that in the presence of leukemia inhibitory factor (LIF) they can be maintained and proliferated in a pluripotent stage (Smith et al., Nature 336:688-690, 1988). Today, this is frequently exploited for the genetic modification of ES cells. Blastocyst injection of these engineered ES cells is then used to generate transgenic animals (Robertson et al., Nature 323:445-448, 1986). Less frequently, ES cells have been used for in vitro differentiation studies. This technique permits the study and experimental manipulation of early tissue development under controlled conditions in vitro. Meanwhile, pluripotent embryonic stem cells have been isolated from a large variety of species including rat (Iannaconne et al., Dev. Biol. 163:288-292, 1994), hamster (Doetschman et al., Dev. Biol. 127:224-227, 1988), birds (Pain et al., Development 122:2339-2348, 1996), fish (Sun et al., Mol. Mar. Biol. Biotechno. 4:193-199, 1995), swine (Wheeler, Reprod. Fertil. Dev. 6:563-568, 1994), cattle (First et al., Reprod. Fertil. Dev. 6:553-562) and primates (Thomson et al., Proc. Natl. Acad. Sci. USA 92:7844-7848, 1995). Several months following the submission of the German patent application No. 197 56 864.5 two research teams succeeded in isolating ES cells and ES cell-like stem cells from embryonic human tissue (Thomson et al., Science 282: 1145-1147, 1998; Shamblott et al., Proc. Natl. Acad. Sci. USA 95: 13726-13731, 1998). Other recent studies indicate that embryos and embryonic stem cells can be generated by transplanting nuclei from embryonic and mature mammalian cells into enucleated oocytes (Campbell et al., Nature 380: 64-66, 1996; Wilmut et al., Nature 385:810-813, 1997).

During the last couple of years, several research groups succeeded in the in vitro differentiation of ES cells into cells of the nervous system. In most cases neural differentiation was initiated by treating aggregated ES cells with retinoic acid (Bain et al., Dev. Biol. 168:342-357, 1995; Strübing et al., Mech. Dev. 53:275-287, 1995; Fraichard et al., J. Cell Sci. 108:3181-3188, 1995; Finley et al., J. Neurosci. 16:1056-1065, 1996). Some of the cells differentiated in this manner exhibited properties of neurons (Bain et al., Dev. Biol. 168: 342-357, 1995; Strübing et al., Mech. Dev. 53:275-287, 1995; Fraichard et al., J. Cell Sci. 108:3181-3188, 1995; Finley et al., J. Neurosci. 16:1056-1065, 1996) and glial cells (Fraichard et al., J. Cell Sci. 108:3181-3188, 1995). Retinoic acid-mediated induction of neural differentiation suffers from two major disadvantages. First, neural differentiation occurs only in a fraction of the cells. A sufficient purification of these neural cells has, so far, not been possible. Second, retinoic acids is a strong inducer of ES cell differentiation. Neurons and glial cells differentiated in the presence of retinoic acid have mostly developed beyond the stage of a precursor and entered a postmitotic phase. Therefore, they are of limited value for cell enrichment strategies and transplantation.

An alternative method for the generation of neural precursor from ES cells was reported recently (Okabe et al, Mech. Dev. 59:89-102, 1996). ES cells aggregated to embryoid bodies are plated and cultured in serum-free media for several days. During this time, massive cell death is observed particularly among non-neural cells. At the end of this stage, more than 80% of the cells express nestin, an intermediate filament typically found in neural precursor cells (Frederiksen & McKay, J. Neurosci. 8:1144-1151, 1988; Lendahl et al., Cell 60:585-595, 1990). These precursor cells can be further expanded as a monolayer culture in the presence of basic fibroblast growth factor (bFGF), and, upon bFGF-withdrawal, differentiate into neurons and astrocytes (Okabe et al., Mech. Dev. 59:89-102, 1996). However, the ability of these cells to proliferate in the presence of bFGF is limited, and increasing astrocytic differentiation is observed after only few passages (Okabe, in: Current Protocols in Neuroscience, John Wiley, New York, 1997). After such short proliferation periods the cultures still contain numerous undifferentiated embryonic cells as well as differentiated non-neural cells. Cell populations containing such contaminants are not suitable for reconstructive transplants. Undifferentiated ES cells may generate tumors (teratocarcinomas), and non-neural donor cells may form non-neural tissue within the graft. Up until now there has been no known procedure which permits the generation of ES cell-derived cells with neuronal or glial properties in a purity required for non-tumorigenic transplants in the nervous system and functional activity in vivo such as, for example, remyelination or replacement of lost neurons with recovery of the abnormal behavior elicited by the neuronal loss.

The generation of sufficient numbers of defined neural precursor cells is currently one of the key problems in neural transplantation At present, precursor cells are isolated from the embryonic mammalian brain. For example, material from up to seven human embryos is required for transplantation of an individual Parkinson patient. Such a strategy is associated with severe problems and cannot be used to treat large numbers of Parkinson patients in the long term. Efforts to proliferate neural cells in vitro prior to transplantation have, so far, not lead to significant improvements. Oncogene-mediated immortalization bears considerable risks due to the introduction of a tumorigenic gene into the donor cells. The order of magnitude of growth factor-mediated proliferation of precursor cells is not sufficient for a potential clinical application. In addition, the ability of expanded cells to incorporate into the host tissue is currently unclear.

ES cells represent an interesting alternative donor source for neural transplants. Their key advantage is that they can be multiplied over long periods of time in an undifferentiated, pluripotent stage (Slack, in: From Egg to Embryo, Cambridge University Press, Cambridge, 1991). During proliferation they maintain their ability to differentiate into all tissues, including neural tissue. However, so far it was not possible to differentiate them selectively into neural precursor cells. Attempts to induce neural differentiation with retinoic acid always yielded mixed cell populations with the neural cells representing only a fraction of the cells (Bain et al., Dev. Biol. 168:342-357, 1995; Strübing et al., Mech. Dev. 53:275-287, 1995; Fraichard et al., J. Cell Sci. 108:3181-3188, 1995; Finley et al., J. Neurosci. 16:1056-1065, 1996). In addition, there have been reports on retinoic acid induced formation of ES cell-derived neurons but not on retinoic acid-induced neural precursors. In a study by Dinsmore et al., such mixed populations were grafted into the brain of quinolinic acid-lesioned rats. Quinolinic acid is a neurotoxin which damages and destroys neurons. Following transplantation some of the grafted cells maintained their neuronal phenotype. However, functional innervation of the host brain or reconstitution of lost brain functions were not observed in these experiments (Dinsmore et al., Cell Transplant. 5:131-143, 1996). The culture method described by Okabe et al. comprises plating of embryoid bodies in ITSFn medium and does not depend on retinoic acid. This method yields up to 85% cells expressing the neural precursor cell marker nestin (Okabe et al., Mech. Dev. 59:89-102, 1996). However, the purity of these cell populations, too, is not sufficient to be used for reconstructive purposes. For example, grafted ES cell-derived precursors cultured in ITSFn medium have been shown to form primitive neuroepithelial structures as well as non-neural tissue such as cartilage and adenoid tissue. It is possible to further proliferate cells cultured in ITSFn in the presence of bFGF. However, the cells rapidly loose their multipotency and, within a few passages, differentiate predominantly into astrocytes. Within this short time span it has not been possible to separate non-neural cells from neural precursor cells. Another major disadvantage of this paradigm is the lack of efficient generation of oligodendrocytes. For example, Okabe et al. observed no oligodendroglial differentiation following plain growth factor withdrawal-induced differentiation. Even after addition of the thyroid hormone T3, oligodendroglial antigens were only detected in 1-2% of the cells (Okabe et al., Mech. Dev. 59:89-102, 1996). As far as neuronal differentiation is concerned, the studies reported by Okabe et al. show no evidence for the generation of neurons expressing tyrosin hydroxylase, cholinacetyl transferase or serotonin—compounds that are of great importance for signal transduction between individual neurons. In addition, these studies show no evidence of neurons expressing peripherin. Peripherin is typically expressed in peripheral neurons and in neurons of the brainstem and the spinal cord.

Thus, the challenge for this invention is to provide isolated, purified, non-tumorigenic ES cell-derived precursor cells with neuronal or glial properties, especially purified neurons and glial cells, as well as methods for the production of these precursor cells in virtually unlimited numbers. The generation of such purified precursor cells permits transplantation into the nervous system without tumor formation as well as functional activity in vivo, e.g., remyelination or replacement of lost neurons with improvement of the abnormal behavior resulting from the neuronal loss, and an improvement of the therapy of neural defects. These challenges are met by the patent claims, the description of the invention and the enclosed figures.

DEFINITIONS

As used herein, the following terms and abbreviations will have the meanings indicated:

Astrocyte
Glial cell of the nervous system. Astrocyte processes are part of the blood-brain-barrier which separates the blood system from fluids inside the brain. Little is known about other functions of this cell type.

Autologous
From the same individual (e.g., cells from the same individual).

bFGF
Basic fibroblast growth factor, identical to FGF-2 (fibroblast growth factor 2). A growth factor which stimulates proliferation of neural precursor cells.

CNTF
Ciliary neurotrophic factor.

DMEM/F12
Dulbecco's Modified Eagle medium/Nutrient Mix F12 (1:1). A commercially available cell culture medium which can be used for serum-free cell culture (e.g., from Life Technologies, NO. 11320).

EGF
Epidermal growth factor. A growth factor which stimulates proliferation of neural precursor cells.

Embryoid Bodies
Cellular aggregates growing in suspension. Embryoid bodies can be generated by growing ES cells in bacterial culture dishes. Since they show similarities to early embryos and generate a variety of different tissues they are called embryoid bodies.

ES Cells
Embryonic stem cells. These cells can be isolated from early embryos at the blastocyst stage. They represent pluripotent cells which can generate all tissues and cell types. In cell culture they can be maintained in a pluripotent stage over many passages. ES cells can also be obtained through nuclear transplantation, i.e. transplantation of cell nuclei into enucleated oocytes and subsequent culture to the blastocyst stage. The definition ES cells also includes ES cell-like cells obtained from embryonic germ cells.

Feeder Cells
Cell population which supports the growth of another cell population. ES cells, for example, are frequently cultured on a feeder layer of embryonic fibroblasts.

ITSFn and N3FL
Cell culture media derived from DMEM/F12 media (Okabe et al., Mech. Dev. 59:89-102, 1996).

LIF
Leukemia Inhibitory Factor. A factor which inhibits differentiation of ES cells.

Neural Precursor
Immature cell of the nervous system which has the potential to develop into mature nervous system cells such as neurons and glia (astrocytes and oligodendrocytes).

Neural Spheres
Cellular aggregates, obtained through proliferation of neural precursor cells in growth factor-containing cell culture media in uncoated cell culture dishes.

Oligodendrocyte
Glial cell of the nervous system. The most important known function of these cells is the insulation of nerve cell processes (axons). Axons are insulated by a sheath of myelin generated by the oligodendrocytes. Defects in myelin formation result in demyelinating diseases. One of the most frequent demyelinating diseases is multiple sclerosis (MS).

PDGF
Platelet-derived growth factor. A growth factor that may, for example, in combination with other growth factors, stimulate proliferation of neural precursor cells. PDGF-A and PDGF-B subunits form dimers known as PDFG-AA, PDGF-AB and PDGF-BB.

Pluri-, Multi- and Bipotent Cells
Precursor cells which have the potential to differentiate into many different (pluri- and multipotent) or two different (bipotent) mature cell types. In neurobiology, bipotential cells are frequently used as a term for precursor cells which can generate astrocytes and oligodendrocytes.

RT
Room temperature.

Thus, the invention relates to isolated, non-tumorigenic ES cell-derived precursors with neuronal or glial properties, preferably precursor cells which contain no more than 15% primitive embryonic and non-neural cells. In a preferred embodiment the cells are grown as monolayers or spheres. In a particularly preferred embodiment the cells show neuronal, astrocytic and/or oligodendroglial properties. In another preferred embodiment the precursor cells are derived from ES cells isolated from blastocysts which were generated by nuclear transplantation into oocytes. In another preferred embodiment the precursor cells are derived from embryonal stem cells generated from embryonic germ cells. In another preferred embodiment the precursor cells are derived from mammalian ES cells or mammalian oocytes. In another preferred embodiment the precursor cells are derived from mouse, rat, hamster, sheep, swine, cattle, non-human primates and humans. In a particularly preferred embodiment the precursor cells are genetically modified. In another particularly preferred embodiment the precursor cells are maintained in a frozen condition. In another particularly preferred embodiment the precursor cells are used to generate cell libraries composed of autologous and non-autologous precursor cells.

The invention further relates to a method for the generation of purified precursor cells with neuronal or glial properties, comprising the following steps:
(a) proliferation of ES cells
(b) culturing of the ES cells from a) to a neural precursor cell stage
(c) proliferation of the neural precursor cells in growth factor-containing serum-free medium
(d) proliferation of the neural precursor cells from (c) in another growth factor-containing serum-free medium and isolation of the purified precursor cells.
(e) proliferation of the precursor cells from (d) in another growth factor-containing serum-free medium and isolation of the purified precursor cells with neuronal or glial properties.

In a preferred embodiment of the invention, the ES cells from (a) are proliferated to aggregates, especially embryoid bodies. In another preferred embodiment of the invention the growth factor-containing serum-free medium in (c) contains bFGF. In other preferred embodiments the growth factor-containing serum-free media in (d) and (e) contain the growth factor combinations bFGF-EGF and bFGF-PDGF, respectively. In another preferred embodiment the purified neural precursor cells are transferred in a medium suitable for injection.

The invention also relates to a method for the generation of purified precursor cells with neuronal or glial properties, comprising the following steps:

(a') proliferation of ES cells
(b') culturing of the ES cells from (a') to a neural precursor cell stage
(c') proliferation of the neural precursor cells in growth factor-containing serum-free medium
(d') proliferation of the neural precursor cells from (c') in another growth factor-containing serum-free medium to neural spheres and isolation of the neural spheres.
(e') proliferation of the neural spheres from (d') in a growth factor-containing serum-free medium until they form an outgrowth of glial precursor cells and isolation of the purified precursor cells.

In a preferred embodiment of the invention, the ES cells from (a') are proliferated to aggregates, especially embryoid bodies. In an additional step (f'), the glial precursor cells obtained in (e') are guided towards an astrocytic or an oligodendroglial differentiation by adding single factors to the culture medium; then the astrocytic or oligodendroglial cells are isolated. In a preferred embodiment of the invention the growth factor-containing serum-free medium in (c') contains bFGF. In another preferred embodiment the growth factor-containing serum-free media in (d'), (e') and (f') contain the growth factors bFGF and EGF, either alone or in combination. In another preferred embodiment, ciliary neurotrophic factor (CNTF) and thyroid hormone (T3) are used in step (f') to promote astrocytic and oligodendroglial differentiation, respectively. In another preferred embodiment the purified neural precursor cells are transferred in a medium suitable for injection.

The neural precursor cells obtained by the invention may be used as therapeutic tool for medical treatment. A preferred application of the purified neural precursor cells is the generation of therapeutic tools for the treatment of neural defects. A particularly preferred application is the reconstitution of neuronal cells or the remyelination of demyelinated nerve cells, in particular within demyelinated areas of the nervous system, by cell transplantation into the nervous system.

Preferred applications include the reconstitution of neuronal cells damaged or lost as result of traumatic, ischemic, degenerative, genetic, hypoxic, metabolic, infectious, neoplastic or toxic disorders of the nervous system. Particularly preferred is the reconstitution of neural cells in traumatic lesions of the brain and spinal cord, ischemic and hemorrhagic infarctions, Parkinsons disease, Huntingtons disease, Alzheimers disease, hereditary atrophic disorders of the cerebellum and brain stem, motoneuron diseases and spinal muscular atrophies. Preferred applications further include the reconstitution of neuronal cells lost or damaged due to age-related changes. A particularly preferred application is the remyelination of demyelinated areas of the nervous system, particularly in diseases such as multiple sclerosis (MS), adrenoleukodystrophy and Pelizeaus-Merzbacher disease.

Another preferred application of the ES cell-derived neural precursor cells is cell-mediated gene transfer into the nervous system. Preferred applications for cell-mediated gene transfer include hereditary metabolic disorders due to enzyme deficiencies and neoplastic disorders of the nervous system. The ES cell-derived neural precursor cells obtained through this invention may also be used for the in vitro production of factors, e.g., polypeptides, for clinical and commercial applications.

DESCRIPTION OF THE FIGURES

FIG. 4. Vibratom sections taken from a recipient brain following transplantation of ES cell-derived glial precursors.

Figure 1:
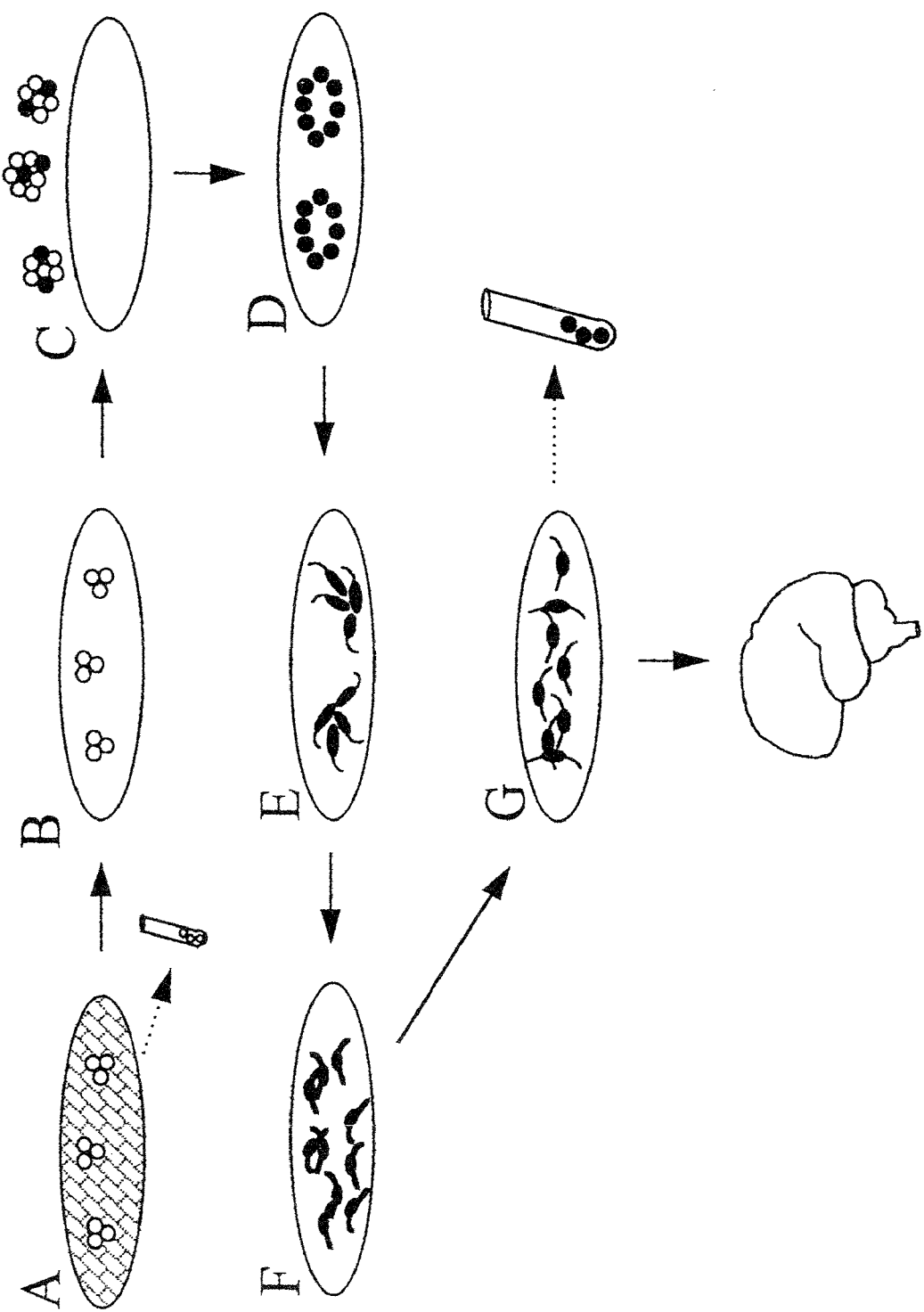
FIG. 1 is a schematic representation of the generation of ES cell-derived neural precursors. (A) ES cells (circles) proliferating on a feeder layer of embryonic fibroblasts (squares). Following proliferation the ES cells may be further propagated or frozen in liquid nitrogen. (B) ES cells growing in gelatin-coated cell culture dishes without feeder cells. (C) Embryoid bodies with incipient differentiation in neural cells (black circles). (D) Plated embryoid bodies growing in ITSFn medium. This medium favors the survival of neural cells (black circles). (E) ES cell-derived neural precursor cells proliferating in a growth factor-containing serum-free medium in the presence of bFGF (N3FL medium). (F) ES cell-derived neural precursor cells proliferating in a growth factor-containing serum-free medium in the presence of bFGF and EGF (N3EFL medium). (G) ES cell-derived neural precursor cells proliferating in a growth factor-containing serum-free medium in the presence of bFGF and PDGF (N2FP medium). After two passages in N2FP medium the cells may be used for remyelinating transplants. Alternatively they may be frozen in serum-free freezing media for later use.
Figure 2:
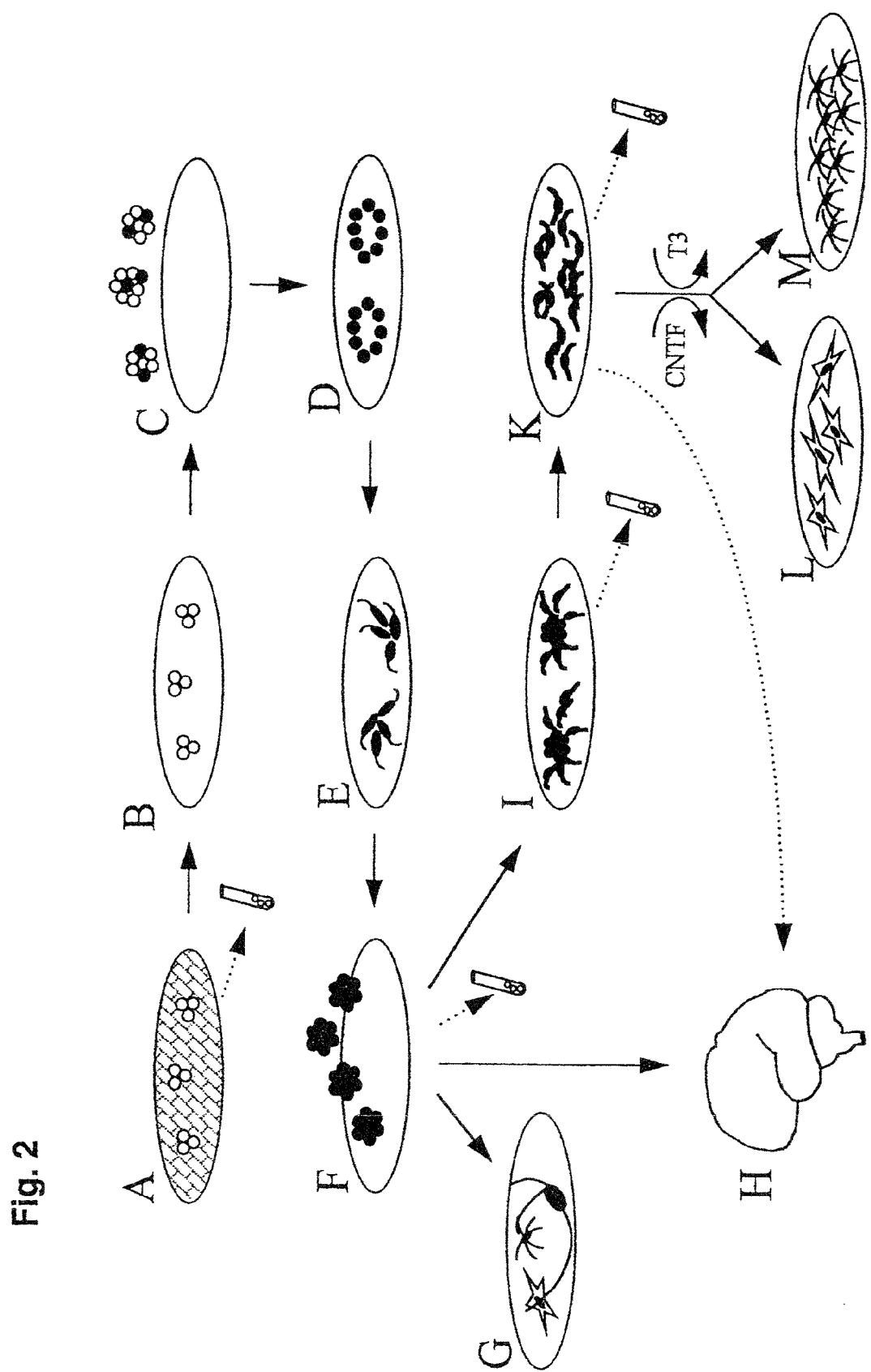
FIG. 2 is a schematic representation of the generation of neural spheres and sphere-derived cell populations from ES cells. Steps (A) to (E) are identical to FIG. 1. (F) Neural spheres generated from N3FL cultures, proliferating in growth factor-containing serum-free medium in the presence of bFGF and EGF (N2EF medium). Cells at this stage may be cryopreserved. (G) In vitro differentiation of ES cell-derived neural spheres induced by growth factor withdrawal. The spheres give rise to neurons, astrocytes and oligodendrocytes. (H) Transplantation of ES cell-derived neural spheres into the nervous system. (I) Generation of glial precursor cells from plated ES cell-derived neural spheres (Touch-down cultures). The ES cell-derived neural spheres are propagated in the presence of growth factors until they start adhering to the uncoated cell culture dishes. At this point, glial precursor cells migrate out of the spheres onto the cell culture dish. (K) Following removal of the spheres, the sphere-derived glial precursors are further proliferated in the presence of growth factors. Cells generated in (I) and (K) can be cryopreserved, and the glial precursor cells obtained in (K) may be used for transplantation into the nervous system. (L) and (M) Addition of CNTF and T3 during growth factor withdrawal promotes astrocytic (L) and oligodendroglial (M) differentiation of the ES cell-derived glial precursors.
Figures 3A, 3B, 3C, 3D, 3E, 3F, 3G, 3H:
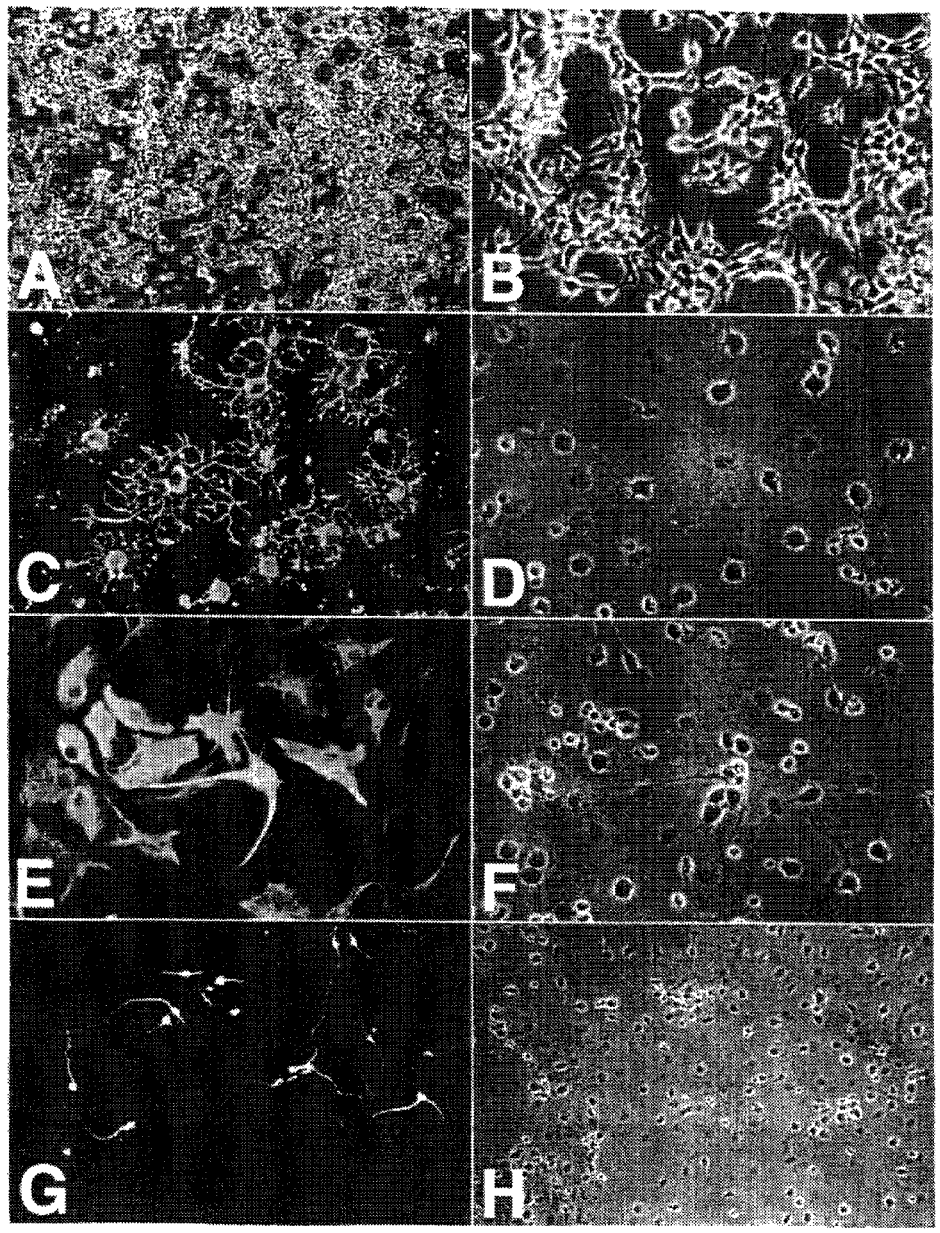
FIG. 3 shows cultures of neural precursor cells following in vitro proliferation and differentiation of ES cells. (A-B) Phase contrast pictures of neural precursor cells derived from J1 ES cells proliferating in N2FP medium. (C-D) Oligodendroglial differentiation of N2FP cultures four days after withdrawal of bFGF and PDGF. Numerous cells express the oligodendroglial marker antigen 04. Corresponding immunofluorescence and phase contrast pictures are shown in C and D, respectively. (E-F) Astrocytic differentiation of N2FP cultures. Four days after growth factor withdrawal numerous GFAP-positive astrocytes can be detected. Corresponding immunofluorescence and phase contrast pictures are shown in E and F, respectively. (G-H) Neuronal differentiation of N2FP cultures. In addition to oligodendrocytes and astrocytes, neurons can be detected following growth factor withdrawal. They exhibit long processes and prominent expression of the neuronal marker antigen beta-III-tubulin. Corresponding immunofluorescence and phase contrast pictures are shown in G and H, respectively.

Following transplantation into a fetal rat brain, the glial precursor cells differentiate into oligodendrocytes and astrocytes. The ES cell-derived oligodendrocytes myelinate the host brain. (A) Following intraventricular transplantation into a fetal rat brain, donor-derived astrocytes migrate into the brain tissue. In this experiment, single cell suspensions of N2FP cultures were injected into the ventricular system of 17-day-old rat embryos. Recipient animals were analysed three weeks after birth. An antibody to the mouse-specific glial antigen M2 was used to detect donor-derived cells. The third ventricle is visible in the upper half of the microscopic field. (B) Incorporation of ES cell-derived glial cells in the cerebral cortex of a neonatal rat. Cells were implanted into the host ventricle at embryonic day 16. Immunofluorescent analysis using an antibody to the mouse-specific antigen M6. The cells exhibit a characteristic astroglial morphology. (C) Incorporation of ES cell-derived oligodendrocytes into the tectum (colliculus inferior) of a 22-day-old myelin-deficient rat which had received an intraventricular injection of an N2FP culture on embryonic day 17. Donor cells were identified using DNA in situ hybridisation with a DNA probe to mouse satellite DNA (black nuclear label). The incorporated cells have initiated myelination of the host brain. Since myelin-deficient rats lack PLP immunoreactivity in the central nervous system, myelination can be detected using an antibody to PLP (dark processes). (D) High power view of an ES cell-derived myelinating oligodendrocyte following incorporation into the hypothalamus of a 22-day-old recipient animal. The cell shows nuclear hybridization signal and PLP-positive processes in a typical parallel orientation.

FIG. 5. Cultures of ES cell-derived neural spheres and sphere-derived cell populations. (A) 5-day-old neural spheres, derived from the ES cell line J1. Spheres at this stage may be used for transplantation into the nervous system. (B) Two-week-old neural spheres, derived from J1 ES cells, were stained with an antibody to nestin, an intermediate filament typically expressed in neural precursor cells. At this stage, the neural spheres are macroscopically visible (immunofluorescence picture). (C-D) Five-day-old neural spheres, derived from CJ7 ES cells, were plated in cell culture dishes plated with polyornithine and fibronectin and cultured for another five days in the absence of growth factors. The spheres have disintegrated and differentiated into neural cells. (D) shows a double immunofluorescence analysis using antibodies to the neuronal antigen beta-III-tubulin (bright signal) and the neural precursor cell marker nestin (dark signal, arrows). The comparison with the corresponding phase contrast picture (C) reveals that all cells depicted in this field express either of the two markers. (E-F) Culture of 5-day-old ES cell-derived neural spheres (derived from the ES cell line J1) differentiated for another 7 days on polyornithine and fibronectin in the absence of growth factors and stained with antibodies to the neuronal marker microtubule-associated protein 2 (MAP2; E) and the neurotransmitter GABA (F). These immunofluorescent micrographs show that numerous neurons express the neurotransmitter GABA. Cell populations enriched in GABAergic cells may be used for neural transplantation in patients with Huntingtons disease. (G-H) Cells from the same cell culture experiment, stained with antibodies to the neuronal marker MAP2 (G) and the neurotransmitter glutamate (H; G and H are immunofluorescence micrographs). Numerous neurons express the neurotransmitter glutamate. (I) Culture of 5-day-old ES cell-derived neural spheres (derived from the ES cell line J1) differentiated for another 2 weeks on polyornithine and fibronectin in the absence of growth factors and double labeled with antibodies to the neuronal marker antigens beta-III-tubulin (filamentous staining in cell processes) and synapsin (dotty signal associated with cell processes). To support neuronal differentiation, cells were treated with the neurotrophin brain-derived neurotrophic factor (BDNF; 20 ng/ml) during the last 5 days of in vitro differentiation. The picture demonstrates that neurons generated from ES cell-derived neural spheres develop mature morphologies and express synaptic proteins important for neuronal signaling. (K) Culture of 5-day-old ES cell-derived neural spheres (derived from the ES cell line J1) differentiated on polyornithine and fibronectin in the absence of growth factors and labeled with an antibody to tyrosin hyroxylase. Neurons expressing tyrosin hyroxylase are used for transplantation in patients with Parkinsons disease. This immunofluorescence analysis demonstrates that numerous ES cell-derived neurons express this enzyme. (L) Culture of an 11-day-old ES cell-derived neural sphere (derived from the ES cell line J1) differentiated for another week on polyornithine and fibronectin in the absence of growth factors and labeled with an antibody to the astroglial antigen glial fibrillary acidic protein (GFAP). This immunofluorescence analysis demonstrates that ES cell-derived neural spheres also give rise to astrocytes. (M) Culture of 5-day-old ES cell-derived neural spheres (derived from the ES cell line J1) differentiated for another 5 days on polyornithine and fibronectin in the absence of growth factors and labeled with an antibody to the oligodendroglial marker O4. This immunofluorescence analysis demonstrates that ES cell-derived neural spheres also give rise to oligodendrocytes.

Figure 6A:
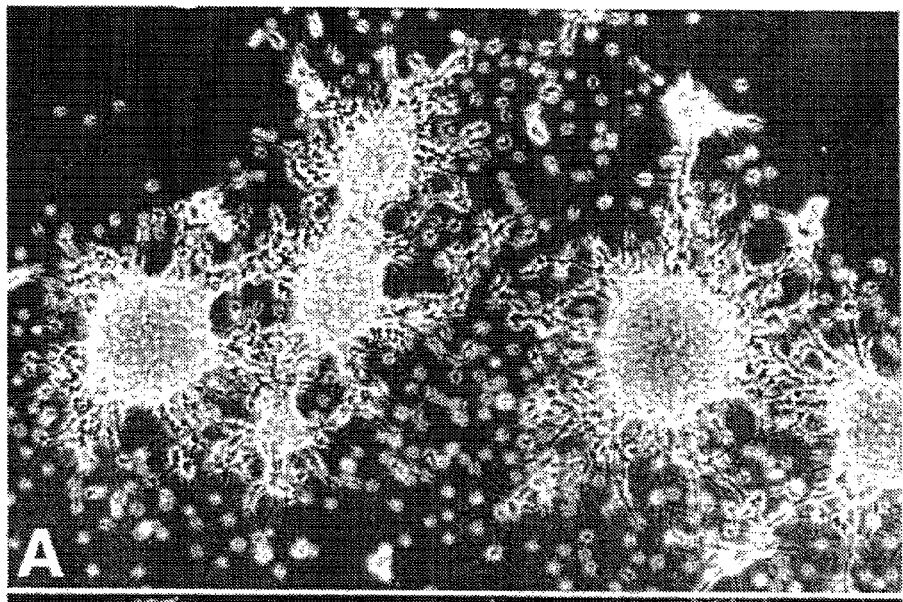
Figure 6B:
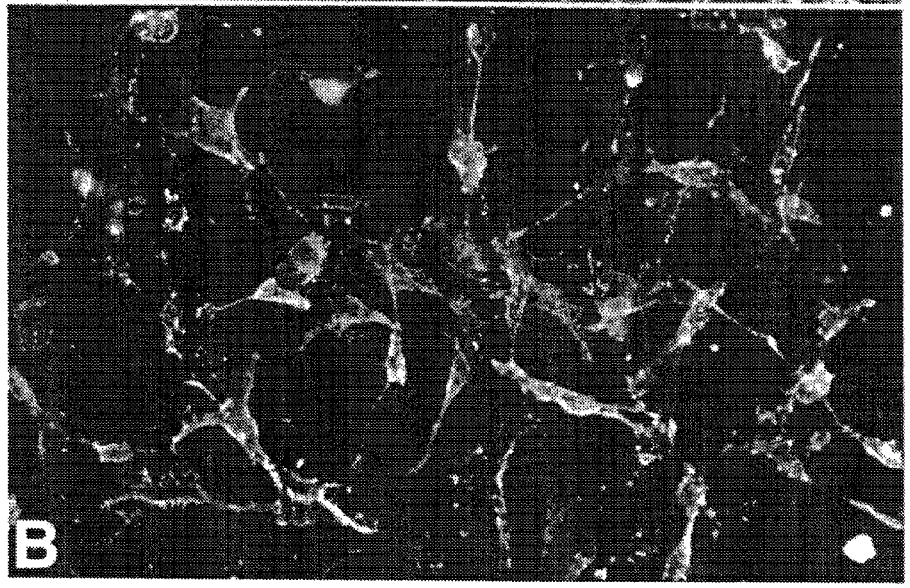

FIG. 6. Glial precursor cells generated from ES cell-derived neural spheres. (A) Typical example of a so-called touch-down culture. Neural spheres derived from the ES cell line J1 adhere to uncoated cell culture dishes and generate an outgrowth of glial cells. The adherent spheres can easily be removed by shaking, leaving behind a monolayer of purified glial precursor cells. (B) Immunofluorescence analysis of a glial precursor cell population generated as touch-down culture from ES cell-derived neural spheres (derived from the ES cell line J1). This immunofluorescence analysis demonstrates that the glial precursor cells express the neural antigen A2B5.

Figures 7A, 7B, 7C, 7D:
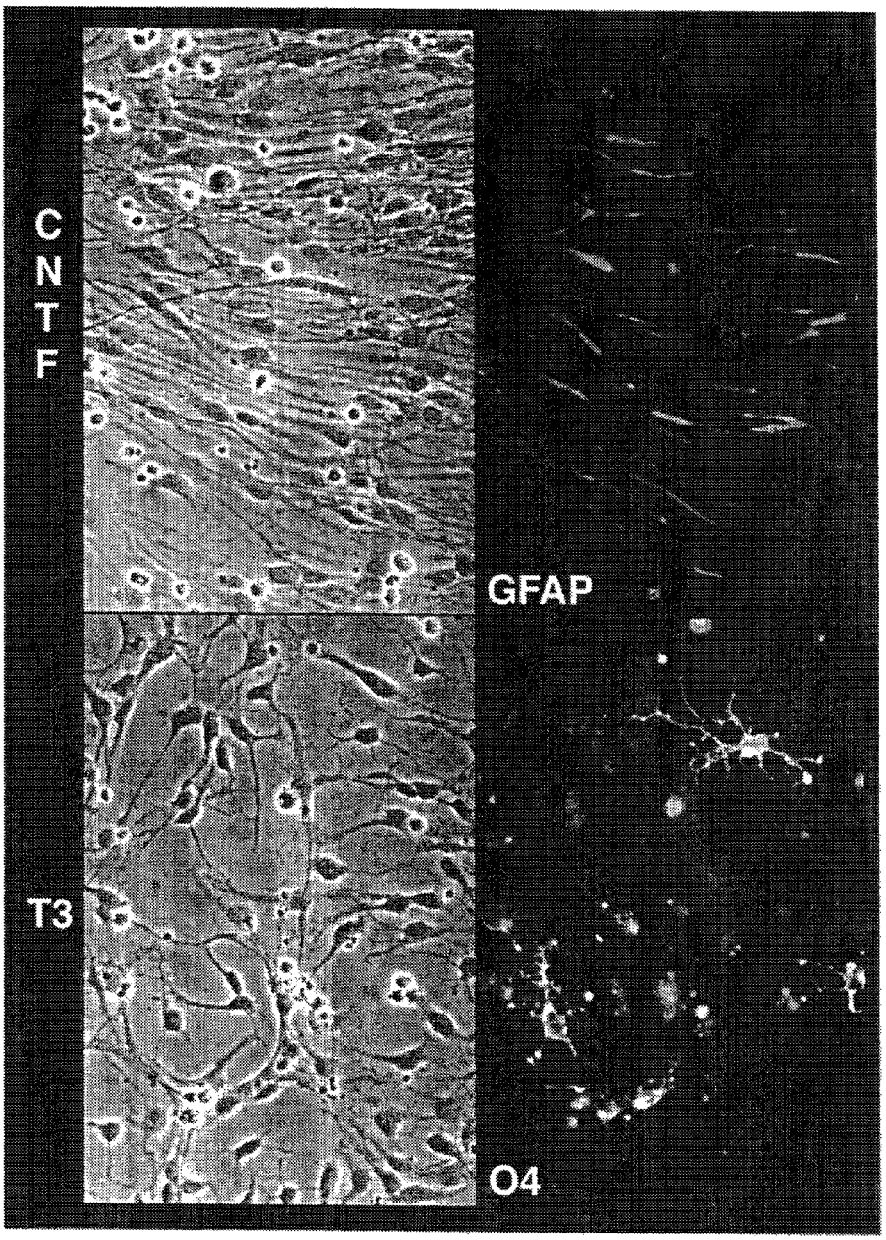

FIG. 7. Targeted differentiation of ES cell-derived glial precursors by addition of single factors. A touch-down culture generated from ES cell-derived neural spheres (derived from the ES cell line J1) and proliferated in the presence of EGF and bFGF was treated with CNTF (10 ng/ml) or T3 (3 ng/ml). Two days later, EGF and bFGF were withdrawn while the cells continued to receive CNTF or T3. After 5 days of growth factor withdrawal, the cells were fixed and stained with antibodies to the astrocytic antigen GFAP and the oligodendroglial antigen O4. The corresponding immunofluorescent and phase contrast pictures demonstrate that addition of CNTF or T3 influences the differentiation of the ES cell-derived precursor cells. In the presence of CNTF, the majority of the cells acquire an astrocytic morphology and express the astrocytic marker GFAP. In the presence of T3, the cells acquire a multipolar oligodendroglial morphology and express the oligodendroglial marker O4.

FIG. 8. Neuronal differentiation of ES cell-derived neural spheres (derived from the ES cell line J1) in vitro (A-B) and following transplantation into the nervous system of ibotenic acid-lesioned rats, an animal model of Huntingtons disease (C-D). Five-day-old neural spheres were grafted into the striatum of adult ibotenic acid-lesioned rats. At the same time, an aliquot of the spheres was differentiated by growth factor withdrawal over 5 days in vitro and subsequently stained with an antibody to the neurotransmitter GABA (A, immunofluorescence; b, corresponding phase contrast image). The figures illustrate that numerous ES cell-derived neurons express the neurotransmitter GABA. Seven weeks after transplantation, a vital transplant exhibiting neuronal differentiation is detected in the adult rat brain (C and D). (C) Low power overview of a transplant which is identified with an antibody to the mouse-specific neural antigen M6 (immunofluorescence). The graft shows homogenous staining and is well integrated in the recipient brain. This animal also showed functional improvement with normalization of the rotation behavior induced by the ibotenic acid lesion. (D) Donor cell-derived axons that have grown from the transplant into the adjacent host brain. Immunofluorescent staining with an antibody to M6.

To start the generation of neural precursor cells, embryonic stem cells, for example of mouse origin, may be proliferated to the desired number in serum-containing medium on a feeder layer of non-mitotic embryonic fibroblasts according to standard methods (Hogan et al., Manipulating the Mouse Embryo, Cold Spring Harbor Press, New York, 1994). In addition to established mouse ES cell lines such as J1 (Li et al., Cell 69:915-926, 1992), R1 (Nagy et al. Proc. Natl. Acad. Sci. USA 90:8424-8428, 1993) and CJ7 (Swiatek & Gridley, Genes Dev. 7:2071-2084, 1993), ES cells may also be obtained from embryos, e.g., from 3 to 4-day-old mouse blastocysts (Hogan et al., Manipulating the Mouse Embryo, Cold Spring Harbor Press, New York, 1994). ES cells may also be obtained from other species such as rat (Iannaconne et al., Dev. Biol. 163:288-292, 1994), hamster (Doetschman et al., Dev. Biol. 127:224-227, 1988), birds (Pain et al., Development 122:2339-2348, 1996), fish (Sun et al., Mol. Mar. Biol. Biotechno. 4:193-199, 1995), swine (Wheeler, Reprod. Fertil. Dev. 6:563-568, 1994), cattle (First et al., Reprod. Fertil. Dev. 6:553-562), primates (Thomson et al., Proc. Natl. Acad. Sci. USA 92:7844-7848, 1995) or from embryonic human tissue. Several months following the submission of the German patent application No. 197 56 864.5 two research teams succeeded in isolating ES cells and ES cell-like stem cells from embryonic human tissue (Thomson et al., Science 282: 1145-1147, 1998; Shamblott et al., Proc. Natl. Acad. Sci. USA 95: 13726-13731, 1998).

More recent studies indicate that embryos and embryonic stem cells can be generated by transplanting nuclei from cells of an mature individuum into enucleated oocytes (Wilmut et al., Nature 385:810-813, 1997). For the specialist it is obvious that a combination of such nuclear transfer strategies with the invention described herein permits the generation of autologous neural precursor cells from differentiated cells of the same individuum. The generation of embryos through transfer of nuclei from mature cells into enucleated oocytes has been applied to large mammals such as sheep (Wilmut et al., Nature 385:810-813, 1997) and is, therefore, also applicable to humans. ES cells or ES cell-like cells may also be obtained from embryonic germ cells. Studies published after the priority date of this patent application show that human ES cells can be isolated from human blastocysts (Thomson et al., Science 282: 1145-1147, 1998), and human ES cell-like cells can be obtained from human primordial germ cells (Shamblott et al., Proc. Natl. Acad. Sci. USA 95: 13726-13731, 1998). These studies indicate that the methods described in this patent application, alone or in combination with nuclear transfer strategies, can also be applied to humans.

Feeder-dependent ES cell lines may be plated in gelatin-coated cell culture dishes and subsequently aggregated in uncoated Petri dishes in the absence of LIF to form embryoid bodies (Okabe et al., Mech. Dev. 59:89-102, 1996). Three to four-day-old embryoid bodies may then be plated in cell culture dishes and grown for four to eight days in serum-free medium (ITSFn medium; Okabe et al., Mech. Dev. 59:89-102, 1996). During this time pronounced cell death can be detected among non-neural cells.

After four to eight days in ITSFn medium the cells may be triturated to a single cell suspension using a small-bore pipette and transferred into N3FL medium. N3FL is a serum-free medium that contains bFGF (Okabe et al., Mech. Dev. 59:89-102, 1996). bFGF is used to promote proliferation of neural precursor cells.

After a 4 to 8-day-period in N3FL medium, the generation of glial and neuronal precursor cell populations is initiated. In contrast to neuronal precursors, glial precursors exhibit a pronounced proliferative potential. The method described herein exploits this proliferative potential. Cells derived from N3FL cultures are sequentially propagated through different serum-free growth factor-containing media. During this stage a strong enrichment of bipotent precursors with astrocytic and oligodendroglial differentiation capacity can be observed. Concomitantly, primitive embryonic cells and non-neural cells are differentiated and eliminated from the cultures. To that end, cells cultured in N3FL medium are harvested mechanically, triturated to a single cell suspension and transferred into a serum-free medium which may contain the growth factors bFGF and EGF (N3EFL medium). In this medium the cells are propagated as monolayer until they become subconfluent. After approximately two passages cells cultured in this medium may be used for transplantation purposes. For further purification, an additional step may be included.

Cells cultured in N3EFL medium may be harvested mechanically, triturated to a single cell suspension and replated in a serum-free medium containing a second growth factor combination, e.g., bFGF and PDGF.

Cells obtained through this protocol may be propagated through further passages in this medium. After approximately two passages, the culture consists of purified neural precursor cells which may be used directly or following isolation, e.g., for remyelinating transplants. At this stage, they form a homogenous layer of cells with a bipolar to multipolar morphology. They may be frozen and thawed at this stage or at earlier stages without loosing their precursor cell properties. If the growth factors are not added for several days, growth factor withdrawal will induce differentiation in vitro. In this case, immunohistochemical analyses show the presence of marker antigens for oligodendrocytes (e.g., 04) and astrocytes (e.g., GFAP) in addition to markers for neural precursor cells (e.g., nestin). 04- and GFAP-positive cells may account for 20-40% and 30-70% of the cell population, respectively. In addition, cells expressing neuronal antigens may be found in these cultures.

The generation of neuronal and glial precursor cells in form of neural spheres is also initiated after a 4 to 8-day-period in N3FL medium. To enrich neural cells, cells grown in N3FL medium are harvested mechanically, triturated to a single cell suspension and further propagated in uncoated cell culture dishes in serum-free medium which may contain the growth factors bFGF and EGF. Within a few days, the cells will form cellular aggregates (neural spheres) which are primarily composed of nestin-positive neural precursor cells. The neural spheres can be further propagated as a suspension culture. In contrast, differentiated neural cells and non-neural cells tend to adhere to the surface of the cell culture dishes.

As soon as small spheres have formed, they are removed from the culture and transferred into new uncoated cell culture dishes. Within a few (5-7) days, the spheres may be used for transplantation purposes. In this case the neural precursors within the spheres differentiate into mature neural cells which innervate the host brain. Small undifferentiated neural spheres may be frozen in liquid nitrogen in serum-free freezing medium and thawed and differentiated at a later time point.

The invention also relates to differentiated neural cells in a sphere composition that may be suitable for transplantation. These cells may be obtained through in vitro differentiation of the ES cell-derived precursor cells with neuronal or glial properties described herein. To induce in vitro differentiation, growth factors are withdrawn and spheres composed of undifferentiated neural precursor cells are plated, e.g., in cell culture dishes coated with polyornithine and fibronectin. In these conditions the spheres rapidly adhere to the surface of the cell culture dish and, in addition to nestin-positive neural precursors, yield neurons, astrocytes and oligodendrocytes. Adhering neurons can be further differentiated to express a variety of neuronal markers, e.g., MAP2, beta-III-tubulin, synapsin, cholinacetyltransferase, tyrosin hydroxylase, GABA, glutamate, serotonin, peripherin and calbindin. Maturation and survival of the differentiated neurons can be enhanced by addition of neurotrophins, e.g., BDNF or neurotrophin 3 (NT-3).

In serum-free medium containing growth factors such as, for example, bFGF and EGF, the ES cell-derived neural spheres may be maintained in suspension culture for several weeks. At that stage, the spheres may grow to a large size easily detectable with the naked eye. In these conditions an increasing level of cell differentiation may be observed within the neural spheres. Thus, these spheres can be used to transplant ES cell-derived neurons even at an advanced stage of differentiation. This is not possible using differentiated ES cell-derived neurons in monolayer culture as harvesting of these cells will invariably lead to major damage of the neuronal processes and destruction of the neuronal cell bodies.

During the last couple of years numerous factors have been identified which influence the differentiation of neuronal cell populations. These factors may, for example, lead to polarization within neural tissue. For example, it was shown that the product of the gene Sonic hedgehog induces a ventral phenotype in neural tissue (Ericson et al., Cell 81:747-756, 1995). It is to be expected that such factors also influence the differentiation of neural cells generated artificially from ES cells. For the specialist it is obvious that the application of such factors will permit the generation of neurons and glial cells with specific phenotypes. For example, induction of a ventral mesencephalic phenotype may yield cells suitable for transplantation into Parkinson patients. In cultured fragments of neural tissue it has already been shown that Sonic hedgehog can induce dopaminergic ventral mesencephalic neurons (Wang et al., Nature Med. 1:1184-1188, 1995).

For the generation of glial precursor cells from ES cell-derived neural spheres, the spheres are propagated in suspension in growth factor-containing serum-free medium until they start adhering to the uncoated surface of the cell culture dish. During this phase, bFGF and EGF, individually or in combination, may be used as growth factors. Following adhesion of the spheres, cells with glial morphology migrate from the spheres onto the surface of the cell culture dishes (so-called touch-down cells). The precise development of this cell population is not understood. Presumably, increasing cell differentiation within the spheres leads to formation of glial precursors which exhibit enhanced adhesion and migration behavior. Spheres producing touch-down cells may be used as generators for glial precursors. To that end, spheres generating glial precursors are cultured only for short periods of time (<1 day) in uncoated cell culture dishes. As soon as glial cells have adhered, the spheres are mechanically detached from the dish and transferred into another dish. This will yield ring-shaped monolayers of glial precursors which can be further proliferated in the presence of growth factors, e.g., bFGF and EGF (applied individually or in combination).

'Touch-down cells' generated in this manner express the neural antigen A2B5 (Eisenbarth et al., Proc. Natl. Acad. Sci. USA 76:4913-4917, 1979) and, upon growth factor withdrawal, differentiate into astrocytes and oligodendrocytes. Using immunohistochemical methods, marker antigens for oligodendrocytes (e.g., 04) and astrocytes (e.g., GFAP) can be detected in these differentiated cells. Undifferentiated touch-down cells may be frozen in liquid nitrogen in serum-free freezing medium without loosing their proliferation and differentiation potential. Glial precursor cells generated in this manner may also be used for transplantation in the nervous system.

The differentiation of the ES cell-derived glial precursors can be influenced by addition of single factors. Addition of CNTF (ciliary neurotrophic factor) shortly before und during growth factor withdrawal will promote astrocytic differentiation. Addition of the thyroid hormone T3 during this stage will result in enhanced differentiation of oligodendrocytes. Addition of serum-containing media during or after growth factor treatment results in a strong increase in the number of astrocytic cells in these cultures.

For the specialist it is obvious that the frozen neural precursor cells may, after thawing, also be used for transplantation. Cells frozen at earlier stages of the in vitro differentiation process may be thawed in a standard manner and further propagated and passaged until a homogenous population of bi- and multipolar cells is obtained.

The methods described herein may further be combined with established cell separation cell sorting procedures. For example, neural subpopulations may be separated at defined time points using fluorescent-activated cell sorting (FACS), immunopanning, or similar methods. A detained sorting and subclassification may permit the generation of replacement cells (including genetically modified replacement cells) tailored to the individual patients needs. Since both ES cells and the ES cell-derived neural precursor cells described herein can be frozen and thawed without loosing their properties, it is possible to establish cell banks, including autologous cell banks.

The methodology described herein permits the generation of neural precursor cells, e.g. neuronal, astrocytic and oligodendroglial cells, in a purity and in quantities required, e.g., for the repair of defects in the nervous system. Cells generated with the methodology described herein contain, for example, only few or no primitive embryonic and non-neural cells. The purity of the neural precursor cells described herein far exceeds the purity of approximately 85% which was previously described by Okabe et al. (Mech. Dev. 59:89-102, 1996). The methodology described herein permits the generation of neural precursor cells in a purity of up to 100%. In addition, the methodology described herein permits the generation of large numbers of neural precursor cells without depending on brain tissue. The neural precursor cells described herein may be obtained from ES cells of various species, e.g., mouse, rat, hamster, birds, fish, swine, cattle, primate or humans. Both, established ES cell lines and ES cells derived from embryos may be used. In addition, the ES cells may be derived from proliferated oocytes. The oocytes may be enucleated and implanted with a cell nucleus derived, for example, from differentiated tissue, permitting the generation of autologous oocytes and ES cells. ES cells or ES-like cells may also be obtained from embryonic germ cells. The ES cells may be genetically modified with standard procedures. For example, a defective gene may be replaced by its 'normal' counterpart using homologous recombination. In addition, genes may be deleted using standard methods. These procedures have been extensively used in mice and are, therefore, state of the art.

The rapid proliferation of ES cells and their amenability to genetic modification permits the generation of large numbers of genetically modified neuronal and glial precursor cells. Combined with the extensive migration potential of neuronal and glial precursor cells, this permits the population of large areas of the nervous system with genetically modified precursor cells which may substitute missing factors or secrete polypeptides designed for neuroprotection or other applications. Genetic modification of the cells may also be used to remove genes encoding surface antigens which are involved in transplant rejection. Such a strategy may permit a broad clinical application of ES cell-derived precursor cells without the need for immunosuppression.

The neural precursor cells described herein may also by used as therapeutic medical tools for the treatment of neural defects. A typical example for the application of the neural precursor cells described herein is the reconstitution of lost or functionally impaired neurons by transplanted neural precursor cells.

In order to replace lost neurons and to improve neurological deficits associated with this loss, neural spheres described herein may, for example, be grown for 4-7 days in suspension and then implanted into brain regions exhibiting neuronal loss. Six weeks following transplantation, differentiated neurons innervating the host brain may be observed. Donor-derived axons extending into the host brain tissue may, for example, be detected with antibodies to donor-specific neural antigens. The neuronal reconstitution also leads to functional improvement. This may be demonstrated in behavioral tests in ibotenic acid-lesioned rats before and after transplantation. To that end, large numbers of striatal neurons are destroyed by stereotaxic injection of the neurotoxin ibotenic acid. The resulting defect shows similarities to Huntingtons disease. This experimental model is, therefore, frequently used as an animal model of this disease. After unilateral ibotenic acid lesion, the operated animals exhibit a functional asymmetry and a quantifiable abnormal rotation behavior which may be induced by certain drugs, e.g., amphetamine. A transplant rich in neuronal cells may normalize the rotation behavior. This normalization appears to depend particularly on the number of GABAergic neurons within the transplant. The ibotenic acid lesion model and the functional evaluation of neural transplants by analysis of the rotation behavior have been described extensively (Björklund et al., in: Functional Neural Transplantation, Seiten 157-195, Raven Press, New York, 1994). Transplantation of the neural spheres described herein into the brain of ibotenic acid-lesioned rats results in significant postoperative improvement of the abnormal rotation behavior induced by the ibotenic acid lesion. Transplants of, e.g., neural cells into the human nervous system are already being performed in patients (Olanow et al., TINS 19:102-109, 1996).

The glial precursor cells described herein, obtained either from neural spheres or monolayer cultures, may also be used as a tool for the therapy of neural defects. A typical example for the application of the glial precursor cells described herein is the remyelination of demyelinated brain regions by cell transplantation. Since the glial precursor cells described herein exhibit a pronounced migratory potential, they may be used for the treatment of demyelinating diseases encompassing large areas of the CNS. In this case a localized injection of the cells may suffice to populate and remyelinate large areas of the CNS. A typical example of a disease which might be treated in this manner is multiple sclerosis (MS), a disease of unknown cause which is typically associated with multiple foci of demyelination in different regions of the CNS. Transplantation of the neural precursors described herein may be used to remyelinate such defects. In this case the pronounced migration potential of the neural precursor cells may be exploited to target and repair numerous areas of demyelination from single or few implant sites.

In order to myelinate myelin-deficient brain regions, cells derived from monolayer cultures or from ES cell-derived neural spheres may be propagated in growth factor-containing media, harvested mechanically and triturated to a single cell suspension. Transplantation of such cell suspensions into myelin-deficient brain regions typically yields donor-derived astrocytes and oligodendrocytes which are easily detectable by approximately three weeks post transplantation. The transplanted cells typically enwrap host axons with myelin sheaths. Using immunohistochemical methods, myelin proteins such as myelin basic protein (MBP) and proteolipid protein (PLP) can be detected in these myelin sheaths.

The ES cell-derived neural precursors described herein may also be used for the in vitro generation of polypeptides for clinical and commercial applications.

The following examples illustrate how this invention may be used for the generation and transplantation of ES cell-derived neural precursors.

EXAMPLE 1

1.1. ES Cell Proliferation

ES cells (Line J1; Li et al., Cell 69:915-926, 1992) are proliferated on a layer of non-mitotic mouse embryonic fibroblasts in DMEM medium (Life Technologies No. 11965) containing 20% fetal calf serum (FBS, Life Technologies No. 10119) and 1.000 U/ml LIF (Life Technologies No. 13275) according to standard methods (Hogan et al., Manipulating the Mouse Embryo, Cold Spring Harbor Press, New York, 1994). In addition to FBS and LIF, this medium contains standard concentrations of non-essential amino acids (Life Technologies No. 11140; Okabe et al., Mech. Dev. 59:89-102, 1996), adenosine (Sigma No. A-4036), guanosine (Sigma No. G-6264), cytidine (Sigma No. C-4654), uridine (Sigma No. U-3003), thymidine (Sigma No. T-1895) as well as 0.1 mM 2-mercaptoethanol (Sigma No. M-7522), 10 mM L-glutamine (Sigma No. G-5763) and 25 mM HEPES (Sigma No. H-0763). During this and all following stages the cells are cultured in a humidified incubator (humidity>85%) at 37° C. in 5% $CO_2$.

1.2. Removal of Feeder Cells

As soon as the ES cells reach subconfluency, they are washed once with 0.04% EDTA in PBS and subsequently harvested by addition of 0.05% trypsin (Life Technologies No. 35400) and 0.04% EDTA in PBS. Cells are triturated several times through a Pasteur pipette to obtain a single cell suspension. The trypsin is neutralized by the addition of an equal amount of the serum-containing medium used for proliferating the ES cells. Following centrifugation at 300×g for 5 min at RT, cells are plated on gelatin-coated cell culture dishes (Sigma No. G-2500) at a density of approximately $6 \times 10^6$ cells/6 cm dish and further proliferated in the medium used in step 1.1.

1.3. Generation of Embryoid Bodies

As soon as the cells have become subconfluent (i.e., after approximately 2-3 days), they are detached from the gelatin by addition of 0.05% trypsin and 0.04% EDTA in PBS (e.g., 1.5 ml per 6 cm dish). Following detachment, the trypsin is neutralized by addition of 10% FBS in DMEM (e.g., 6.5 ml per 6 cm dish; this medium is equivalent to the medium used in 1.2 but contains only 10% FBS and no LIF). The cell suspension is then plated, e.g., onto 8 uncoated Petri dishes (Nunc No. 240045) and further propagated in DMEM/10% FBS (e.g., 4 ml per 6 cm dish).

1.4. Plating of Embryoid Bodies

After 3-4 days, the embryoid bodies are transferred into a 50 ml tube and collected by sedimentation (1×g; 5 min). The supernatant is discarded and the embryoid bodies are plated into 10 cm cell culture dishes. The plated embryoid bodies should cover approximately 50% of the surface of the cell culture dish. Typically, embryoid bodies collected from 4-6 Petri dishes will suffice to plate one 10 cm dish. Embryoid bodies are cultured overnight in DMEM/10% FBS (10 ml per 10 cm dish).

1.5. Transfer into ITSFn Medium

One day after plating, embryoid bodies attached to the cell culture dish are washed 3 times in DMEM/F12 (Dulbecco's Modified Eagle Medium/Nutritient Mix F12 (1:1); Life Technologies, No. 11320). 10 ml of ITSFn medium are added to each 10 cm dish. This medium contains DMEM/F12, 5 µg/ml insulin (Intergen No. 540101), 50 µg/ml apo-transferrin (Intergen No. 445275), 30 nM selenium chloride (Sigma No. S-5261), 5 µg/ml fibronectin (Life Technologies No. 33010) and penicillin/streptomycin (100 IU/ml/100 µg/ml; Life Technologies No. 15140). Cells are propagated in this medium for 4-7 days, and the medium is replaced every two days. During this time massive cell death can be observed among non-neural cells. In addition, neural precursor cells will appear and form small cell clusters This method of establishing ITSFn cultures has been described previously (Okabe et al., Mech. Dev. 59:89-102, 1996).

1.6. Transfer into N3FL Medium

Cells cultures in ITSFn medium are harvested with 0.05% trypsin and 0.04% EDTA in PBS. The trypsin is neutralized by adding an equivalent amount of serum-containing medium (DMEM/10% FBS). Following centrifugation (300×g; 5 min, RT), cells are resuspended in calcium- and magnesium-free Hanks' Buffered Salt Solution (CMF-HBSS, Life Technologies No. 14180) containing 0.1% DNase (Worthington No. 2139). A cell pellet obtained from one 10 cm dish may be resuspended in a total volume of 3 ml. The cells are then triturated to a single cell suspension using flame-polished Pasteur pipettes with decreasing pore size (e.g., 0.8 mm, 0.5 mm and 0.2 mm). Remaining cell clusters are collected by sedimentation (1×g, 5 min) and discarded. Following centrifugation (300×g, 5 min, RT), cells are plated at a density of approximately 30,000 cells/cm² onto polyornithine-coated cell culture dishes in DMEM/F12 (1:1; Life Technologies No. 11320), 25 µg/ml insulin, 50 µg/ml human apo-transferrin, 20 nM progesterone (Sigma No. P-8783), 100 µM putrescine (Sigma No. P-5780), 30 nM selenium chloride, 1 µg/ml laminin (Life Technologies No. 23017), penicillin/streptomycin (100 IU/ml/100 µg/ml) and 10 ng/ml human recombinant bFGF (R&D Systems No. 233-FB). This medium is equivalent to the N3FL medium described by Okabe et al. (Okabe et al., Mech. Dev. 59:89-102, 1996). For coating with polyornithine, cell culture dishes are filled with 15 µg/ml polyornithine (Sigma No. P-3655) in H₂O for at least 2 hours. The polyornithine solution is removed and the dishes are washed 3 times with PBS. During culture in N3FL medium, bFGF is added daily to a final concentration of 10 ng/ml. The medium is replaced every two days.

EXAMPLE 2

Generation of Neural Precursor Cells

2.1. Transfer into N3EFL Medium

After 4-5 days in N3FL medium, cells are harvested mechanically using a cell scraper (Costar Nr. 3008). Before scraping, cells are washed 3 times with CMF-HBSS with the last wash containing 0.1% DNase. They are triturated to a single cell suspension with flame polished Pasteur pipettes as described in 1.6. Following centrifugation (300×g, 5 min, RT), cells harvested from one 10 cm dish are plated into approximately 5 polyornithin-coated 10 cm dishes in N3EFL medium. This medium contains DMEM/F12 (1:1), 25 µg/ml insulin, 100 µg/ml transferrin, 20 nM progesterone, 100 µM putrescine, 30 nM selenium chloride, 1 µg/ml laminin, penicillin/streptomycin (100 IU/ml/100 µg/ml), 10 ng/ml human recombinant bFGF and 20 ng/ml human recombinant EGF (R&D Systems No. 236-EG). bFGF and EGF are added daily to a final concentration of 10 ng/ml and 20 ng/ml, respectively. Addition of laminin may be omitted after the second medium change.

2.2. Transfer into N2FP Medium

As soon as the cells are 90% confluent (e.g., after 1-2 weeks), they are harvested with a cell scraper without the use of trypsin and triturated to a single cell suspension using flame-polished Pasteur pipettes. Following centrifugation (300×g, 5 min, RT), cells harvested from one 10 cm dish are plated into approximately 5 polyornithin-coated 10 cm dishes in N2FP medium. This medium contains DMEM/F12 (1:1), 25 µg/ml insulin, 100 µg/ml transferrin, 20 nM progesterone, 100 µM putrescine, 30 nM selenium chloride, penicillin/streptomycin (100 IU/ml/100 µg/ml), 10 ng/ml human recombinant bFGF and 10 ng/ml human recombinant PDGF-AA (R&D Systems No. 221-AA). bFGF and PDGF-AA are added daily and the medium is replaced every two days.

2.3. Passaging Cells in N2FP Medium

As soon as the cells have become subconfluent, they are harvested with a cell scraper without the use of trypsin and passaged at a 1:5 ratio. Usually, no further trituration step is required to obtain a single cell suspension. After at least 2 passages in bFGF and PDGF-containing medium, the cells represent a population of precursors that may be used for remyelinating transplants. Alternatively, the cells may be harvested with a cell scraper without the use of trypsin and cryopreserved in serum-free freezing medium (Sigma No. C-6295) for later use. The purified neural precursors can be isolated and transferred into a medium suitable for injection, e.g., CMF-HBSS (Life Technologies Nr. 14180).

2.4. In Vitro Differentiation of Neural Precursor Cells

For in vitro differentiation, neural precursor cells are harvested with a cell scraper without the use of trypsin and plated into polyornithin-coated cell culture dishes to reach a confluency of approximately 50%. The cells are propagated for another 4-7 days in the medium described in 2.2 but without addition of bFGF and PDGF. The medium is replaced every two days. Cultures are fixed in 4% paraformaldehyde (Sigma No. P-6148) in PBS and subjected to immunofluorescent analysis using antibodies to the oligodendroglial antigen O4 (Boehringer No. 1518925, dilution 1:10) and the astrocytic antigen GFAP (Chemicon, No. AB1980, dilution 1:100). In doing so, we observed that up to 32% of the cells exhibit a typical oligodendroglial morphology with expression of O4 after four days of growth factor withdrawal. At the same time, up to 49% of the cells expressed GFAP. In addition, these cultures contained cells immunoreactive with an antibody to the neuronal antigen beta-III-tubulin (BAbCO, No. MMS-435P-250, dilution 1:500).

EXAMPLE 3

Generation of Neural Spheres and Neural Precursors Thereof 3.1. Generation of Neural Spheres in N2EF Medium After 4-5 days in N3FL medium (s.1.6.), cells are harvested mechanically using a cell scraper (Costar Nr. 3008). Before scraping, cells are washed 3 times with CMF-HBSS with the last wash containing 0.1% DNase. They are triturated to a single cell suspension with flame polished Pasteur pipettes as described in 1.6. Following centrifugation (300×g, 5 min, RT), the cells are plated in uncoated cell culture dishes at a density of 1,200-12,000 cells/cm$^2$ in N2EF medium. This medium contains DMEM/F12 (1:1), 25 µg/ml insulin, 100 µg/ml transferrin, 20 nM progesterone, 100 µM putrescine, 30 nM selenium chloride, penicillin/streptomycin (100 IU/ml/100 µg/ml), 20 ng/ml human recombinant bFGF and 20 ng/ml human recombinant EGF (R&D Systems No. 236-EG). bFGF and EGF are added daily to a final concentration of 20 ng/ml each, and the medium is replaced every two days. To prevent loss of floating spheres during the media changes, cells are sedimented at 150×g for 3 min at RT. The pellet is resuspended in fresh medium and replated into new uncoated cell culture dishes.

3.2. In Vitro Differentiation of ES Cell-derived Neural Spheres

For in vitro differentiation, five-day-old ES cell-derived neural spheres may be sedimented at 150×g for 3 min at RT, plated in cell cultures dishes coated with polyornithine and fibronectin and cultured in the medium described in 3.1. but without addition of bFGF and EGF. Double coating with polyornithine and fibronectin is performed by first coating the dishes with polyornithine as described in 1.6. The dishes are then washed 3 times with PBS and further incubated for 2-12 hours with PBS containing 1 µg/ml fibronectin. Spheres may be plated immediately after removal of the fibronectin solution. One day after plating, neural spheres typically have attached to the cell culture dish. Following removal of the supernatant, the attached spheres are washed 3 times with fresh medium or CMF-HBSS. Then, new medium is added to the cultures and subsequently replaced every two days.

An immunofluorescent analysis performed on neural spheres fixed five days after plating yielded the following expression profile of neural antigens (mean percentage of labeled cells±SEM): nestin-positive neural precursor cells: 66±3% (antibody from M. Marvin und R. D. G. McKay, NIH, Bethesda, USA, dilution 1:1.000); beta-III-tubulin-positive neurons: 34±3% (antibody from BAbCO, No. MMS 435P-250, dilution 1:500); GFAP-positive astrocytes: 30±2% (antibody from Chemicon, No. AB1980, dilution 1:100); O4-positive cells with oligodendroglial morphology: 6.2±1.7% (antibody from Boehringer, No. 1518925, dilution 1:10).

In addition, neurons generated from 5-day-differentiated ES cell-derived neural spheres expressed microtubule-associated protein 2 (MAP-2, antibodies from Sigma, No. M 4403 und No. M 1406, dilution 1:200) and the neurotransmitters GABA (antibody from Sigma, No. A-2052, dilution 1:700) and glutamate (antibody from Sigma, No. G-6642; dilution 1:700). In some preparations up to 60% of the neurons exhibited a GABAergic phenotype. Immunofluorescent analyses of ES cell-derived neural spheres differentiated in the absence of growth factors for more than 10 days also showed neurons expressing tyrosin hydroxylase (antibody from Eugene, No. TE101, dilution 1:200), cholinacetyltransferase (antibody from Chemicon, No. MAB305, dilution 1:250), serotonin (antibody from Eugene, No. NT102, dilution 1:200), synapsin (antibody from Dr. M. B. Kennedy, Pasadena, Calif., USA, dilution 1:1.000), peripherin (antibody from Chemicon, No. AB1530, dilution 1:1.000) and calbindin (antibody from Sigma, No. C-8666, dilution 1:100). Differentiation and survival of sphere-derived neurons could be promoted by addition of the neurotrophins brain-derived neurotrophic factor (BDNF; 20 ng/ml; Pepro Tech Inc. No. 450-02) and/or neurotrophin 3 (NT-3; Pepro Tech Inc. No. 450-03). ES cell-derived neural spheres differentiated for 10 and more days also contained differentiating oligodendrocytes immunoreactive with an antibody to cyclic nucleotide 3'-phosphodiesterase (CNPase; antibody from Sigma, No. C-5922, dilution 1:200).

3.3. Generation of Glial Precursors from ES Cell-derived Neural Spheres ('Touch-down Cultures')

In order to generate glial precursor cells, spheres propagated in growth factor-containing medium as described in 3.1. are maintained until they start adhering to the uncoated surface of the tissue culture dishes. This usually occurs at day 10-14 of the sphere culture. As soon as a ring-shaped outgrowth is detected around individual spheres, the spheres are detached from the cell culture dish by gentle shaking and removed from the cultures using a pipette. These detached spheres may be plated in new uncoated cell culture dishes to generate further ring-shaped colonies of glial precursor cells. Colonies of glial precursor cells obtained in this manner are further proliferated in the same growth factor-containing medium. Upon reaching 80% confluency, the cells are harvested with a cell scraper without the use of trypsin and replated at a 1:5 ratio. An immunofluorescent analysis revealed that glial precursor cells generated in this manner show strong expression of the neural antigen A2B5 (antibody from Boehringer, No. 1300 016, dilution 1:200). They may be frozen in liquid nitrogen in serum-free freezing medium (Sigma No. C-6295) and subjected to further proliferation, transplantation or differentiation at a later time point.

3.4. Targeted Differentiation of ES Cell-derived Glial Precursors

Targeted differentiation of ES cell-derived glial precursors by single factors was verified by the following experiment:

Glial precursors proliferating in the presence of bFGF (20 ng/ml) and EGF (20 ng/ml) as described in 3.3 were harvested mechanically, passaged onto polyornithin-coated cell culture dishes and propagated until they reached approximately 50% confluency. Cells were then propagated for another two days in the following conditions:

1. continued cultivation in the presence of EGF and bFGF
2. continued cultivation in the presence of EGF and bFGF
3. continued cultivation in the presence of EGF and bFGF with daily additions of CNTF (Regeneron, Inc.; final concentration 10 ng/ml)
4. continued cultivation in the presence of EGF and bFGF with daily additions of T3 (Sigma No. T 6397; final concentration 3 ng/ml)

After 2 days, bFGF and EGF were withdrawn from groups 2, 3 and 4, and the cells were further propagated for 5-7 days with media changes every two days. All cultures were fixed in 4% paraformaldehyde (Sigma No. P-6148) in PBS and subjected to an immunofluorescence analysis with antibodies to the oligodendroglial marker antigen 04 and the astrocytic antigen GFAP. The following expression profiles were obtained for the individual groups (means±SEM):

| | | |
|---|---|---|
| 1. | O4-positive cells with oligodendroglial morphology: | <1% |
| | GFAP-positive cells: | <1% |
| 2. | O4-positive cells with oligodendroglial morphology: | 8.2 ± 2.6% |
| | GFAP-positive cells: | 28 ± 6% |
| 3. | O4-positive cells with oligodendroglial morphology: | 2.6 ± 1.8% |
| | GFAP-positive cells: | 78 ± 2.5% |
| 4. | O4-positive cells with oligodendroglial morphology: | 17 ± 3.6% |
| | GFAP-positive cells: | 39 ± 5.7% |

These data indicate that CNTF and T3 may be used to guide the differentiation of ES cell-derived glial precursors towards the astrocytic and oligodendroglial lineage, respectively.

EXAMPLE 4

Transplantation of Oligodendroglial/Astrocytic Precursors 4.1. Generation of a Cell Suspension for Transplantation The myelination potential of the ES cell-derived glial precursors was verified by the following experiment:

Subconfluent cultures obtained as described in 2.3 were harvested with a cell scraper without the use of trypsin, sedimented by centrifugation at 300×g for 5 min and resuspended in CMF-HBSS containing 0.1% DNase. The cells were triturated to a single cell suspension using flame-polished Pasteur pipettes, counted in a hemocytometer, again sedimented by centrifugation and resuspended at a concentration of approximately 50,000-100,000 cells/µl in CMF-HBSS containing 2 g/L glucose (Sigma No. G-7021). This cell suspension was kept on ice until completion of the transplant experiment (i.e., 4-6 hours).

4.2. Intraventricular Transplantation into the Embryonic Rat Brain

Myelin-deficient rats (Ian Duncan, Department of Medical Sciences, School of Veterinary Medicine, University of Wisconsin-Madison, 2015 Linden Drive West, Madison, Wis. 53706, USA) were used as transplant recipients. A key advantage of embryonic transplantation is that xenotransplants may be performed without eliciting transplant rejection. Myelin-deficient recipient animals offer the advantage that donor-derived myelin can be easily detected. An advantage of the xenograft paradigm is that the transplanted cells can be easily and reliably identified with species-specific DNA probes (Brüstle et al., Neuron 15:1275-1285, 1995). The method of intrauterine transplantation into the embryonic brain is well established (Brüstle et al., Neuron 15:1275-1285, 1995; Brüstle et al., in: Current Protocols in Neuroscience, John Wiley, New York, 1997).

For transplantation, pregnant rats were anesthetized by intraperitoneal injection of ketamine (80 mg/kg) and xylazine (10 mg/kg) at day 16 or 17 of gestation. Following laparotomy, individual embryos were identified under transillumination with a fiber optic light source. The donor cells were loaded in a small glass capillary (pore size 50-100 µm), and the capillary was advanced through the uterine wall and the embryonic skull into the lateral ventricle of the recipient embryo as described (Brüstle et al., Current Protocols in Neuroscience, John Wiley, New York, 1997). Two to nine µl of the cell suspension (containing 100,000 to 900,000 cells) were injected into the ventricular system. Following transplantation of several or all embryos, the abdomen was closed with surgical sutures and the mother animal left for spontaneous vaginal birth. Since myelin-deficiency in this animal model is an X-linked recessive disorder, approximately 50% of the male pups are affected. Affected animals develop strong tremor by the third week of age and usually die within their fourth postnatal week.

4.3. Histological Analysis of the Transplant Recipients

In order to detect donor-derived myelin formation, recipient animals were anesthetized in the third or fourth postnatal week and transcardially perfused with 4% paraformaldehyde (Sigma No. P-6148) in PBS according to standard methods. The brains were removed from the skull, postfixed overnight at 4° C. in the same fixative and subsequently cut in 50 µm sections using a vibratome. Donor cells were detected by DNA in situ hybridization with a probe to mouse satellite DNA (Hörz & Altenburger, Nucl. Acids Res. 9:683-696, 1981; Brüstle et al., Neuron 15:1275-1285, 1995). Donor cell-derived myelin was visualized with antibodies to myelin proteins such as myelin basic protein (MBP; Boehringer No. 1118099) or proteolipid protein (PLP; a gift from Ian Griffiths, Department of Veterinary Clinical Studies, University of Glasgow, Bearsden, Scotland). Sections labeled with antibodies to myelin proteins were subsequently subjected to DNA in situ hybridization with a probe to mouse satellite DNA (Brüstle et al., Neuron 15:1275-1285, 1995). This double labeling procedure permits unequivocal identification of donor cell-derived myelin. The experiments showed that donor cells implanted into the ventricle migrate into a large variety of telencephalic, diencephalic and mesencephalic brain regions (14 analyzed recipient animals). Hybridized cells were found, e.g., in cortex, hippocampus, septum, striatum, bulbus olfactorius, thalamus, hypothalamus, tectum, cerebellum as well as in the corpus callosum, anterior commissure, tractus opticus and the optic nerve. No space-occupying clusters of donor cells were observed after transplantation into the ventricular system. Out of 35 transplanted embryos, 11 male pups exhibited symptoms of myelin deficiency. Eight of these had received successful intraventricular transplants. In six out of these eight animals, donor-derived myelin formation was verified by double labeling of hybridized cells with MBP or PLP-antibodies. In the remaining 2 animals, the number of incorporated cells was too low for a reliable evaluation of donor-derived myelin formation by double labeling procedures. However, immunohistochemical screening of sections from these animals with the mouse-specific antibody M2 (Zhou et al., J. Comp. Neurol. 292:320-330, 1990) also showed incorporated donor-derived glial cells in the host tissue. Donor-derived myelin formation was most pronounced in fiber tracts such as the corpus callosum, the anterior commissure and commissural fibers in tectum. In addition, myelinating donor cells were detected in gray matter regions such as cortex, septum, thalamus, hypothalamus and tectum. Seven out of eight successfully transplanted animals also showed incorporated ES cell-derived astrocytes. Donor-derived astrocytes were detected by immunohistochemistry with antibodies to the mouse-specific antigens M2 (Zhou et al., J. Comp. Neurol. 292:320-330, 1990) and M6 (Lund et al., Neurosci. Lett. 61:221-226, 1985) or by double labeling of cells hybridized with a mouse-specific DNA probe with an antibody to glial fibrillary acidic protein (GFAP; ICN No. 69-110).

EXAMPLE 5

Transplantation of ES Cell-derived Neural Spheres 5.1. Transplantation of ES Cell-derived Neural Spheres into Ibotenic Acid-lesioned Rats To evaluate the potential of the ES cell-derived precursors described herein for the anatomical and functional reconstitution of neuronal cells, 5-day-old neural spheres were generated from the ES cell line J1 as described in 3.1. These spheres were implanted into the striatum of adult Sprague-Dawley rats which had previously been subjected to a stereotaxic injection of the neurotoxin ibotenic acid to induce a unilateral neuronal degeneration in the striatum. This lesion model is well characterized, and the lesion protocol used for these experiments has been published previously (Brüstle et al., in: Current Protocols in Neuroscience, Unit 3.10, John Wiley, New York, 1997). For transplantation, floating spheres were removed from the cell culture dish and transferred into a 50 ml test tube. Following addition of DNase to a final concentration of 0.1%, spheres were sedimented at 150×g for 5 min at RT and subsequently transferred into a 0.5 ml test tube containing 2 g/L glucose (Sigma No. G-7021) in CMF-HBSS. Spheres suspended in this manner were kept on ice until completion of the transplant experiment (up to 4 hours). Recipient animals were anesthetized and the spheres were stereotaxically injected into the striatum. A glass capillary with a pore size of 0.25-0.75 mm was used for injection. This transplantation protocol is well characterized and has been published in detail (Brüstle et al., in: Current Protocols in Neuroscience, Unit 3.10, John Wiley, New York, 1997). A total of 6 recipient animals was used for the experiment. Spheres that had accumulated at the bottom of the test tube were loaded into the glass capillary. Using a stereotaxic frame (Stoelting No. 51600), the cells were injected into the striatum. Spheres were delivered to 2 (n=3) or 5 (n=3) different sites within the lesioned striatum. The following stereotaxic coordinates were used for injection:

| For 2 implantation sites: | | |
|---|---|---|
| Site 1: | teeth holder: | −2.3 mm |
| | anteroposterior orientation: | +0.2 mm (from bregma) |
| | mediolateral orientation: | 3.0 mm (from sagittal suture) |
| | depth of injection: | 5.5 mm (from dura) |
| Site 2: | teeth holder: | −2.3 mm |
| | anteroposterior orientation: | +0.2 mm (from bregma) |
| | mediolateral orientation: | 3.0 mm (from sagittal suture) |
| | depth of injection: | 4.0 mm (from dura) |

| For 5 implantation sites: | | |
|---|---|---|
| Site 1: | teeth holder: | −2.3 mm |
| | anteroposterior orientation: | +0.2 mm (from bregma) |
| | mediolateral orientation: | 3.0 mm (from sagittal suture) |
| | depth of injection: | 6.5 mm (from dura) |
| Site 2: | teeth holder: | −2.3 mm |
| | anteroposterior orientation: | +0.2 mm (from bregma) |
| | mediolateral orientation: | 3.0 mm (from sagittal suture) |
| | depth of injection: | 5.3 mm (from dura) |
| Site 3: | teeth holder: | −2.3 mm |
| | anteroposterior orientation: | +0.2 mm (from bregma) |
| | mediolateral orientation: | 3.0 mm (from sagittal suture) |
| | depth of injection: | 4.0 mm (from dura) |
| Site 4: | teeth holder: | −2.3 mm |
| | anteroposterior orientation: | +1.5 mm (from bregma) |
| | mediolateral orientation: | 2.5 mm (from sagittal suture) |
| | depth of injection: | 6.0 mm (from dura) |
| Site 5: | teeth holder: | −2.3 mm |
| | anteroposterior orientation: | +1.5 mm (from bregma) |
| | mediolateral orientation: | 2.5 mm (from sagittal suture) |
| | depth of injection: | 4.5 mm (from dura) |

10 μl of sphere suspension were transplanted into each site.

To prevent rejection of the xenografts, recipient animals were subjected to immunosuppression. Starting one day before transplantation, the recipient animals received daily intraperitoneal injections of cyclosporin (Sandimmun, Sandoz; 20 mg/kg body weight). To prevent opportunistic infections during immunosuppression, the drinking water was supplemented with tetracyclin (Achromycin, Lederle; final concentration 100 mg/L).

5.2. Analysis of Functional Improvement of the Transplant Recipients

Out of 6 grafted animals, 4 animals survived for more than 4 weeks post transplantation. Analysis of amphetamine-induced rotation behavior in these animals yielded the following values (mean number of rotations per minute):

| Animal No. 200: | 34 days before transplantation: | 9.7 |
|---|---|---|
| | 37 days after transplantation: | 13.9 |
| Animal No. 201: | 24 days before transplantation: | 13.5 |
| | 37 days after transplantation: | 1.3 |
| Animal No. 204: | 43 days before transplantation: | 12.7 |
| | 50 days after transplantation: | 0.5 |
| Animal No. 205: | 86 days before transplantation: | 9.0 |
| | 42 days after transplantation: | 1.0 |

For evaluation of the rotation behavior, the recipient animals received an intraperitoneal injection of D-amphetamine sulfate (Sigma No. A-3278; 5 mg/kg body weight). Starting at 5 minutes after injection, the number of induced rotations was quantified over a 90 min period. The evaluation of amphetamine-induced rotation behavior is an established method for the functional analysis of striatal transplants and has been published extensively (Brüstle et al., in: Current Protocols in Neuroscience, Unit 3.10, John Wiley, New York, 1997). The data show that 3 of the 4 animals show a clear reduction of the lesion-induced rotations.

5.3. Histological Analysis of the Transplant Recipients

For histological analysis, recipient animals were anesthetized 5-9 weeks after transplantation and transcardially perfused with 4% paraformaldehyde in PBS according to standard methods. The brains were removed from the skull, postfixed overnight at 4° C. in the same fixative and subsequently cut into 50 μm sections using a vibratome. Donor cells were detected by DNA in situ hybridization with a probe to mouse satellite DNA (Hörz & Altenburger, Nucl. Acids Res. 9:683-696, 1981; Brüstle et al., Neuron 15:1275-1285, 1995). Hybridized donor cells were detected in the implant sites of all four animals that had been subjected to behavioral analyses (5.2.). Some of the donor cells had migrated from the implant sites into adjacent host brain regions, particularly into the corpus callosum. In animal no. 200, the transplant was localized inside the enlarged lateral ventricle. In this animal, the ibotenic acid injection had resulted in pronounced striatal atrophy with consecutive enlargement of the lateral ventricle. Due to these anatomical changes the transplanted cells had been delivered to the ventricle instead of the striatum. The incorrect localization of the transplant explains the lack of functional improvement in the rotation analyses observed in this animal.

In addition to positive hybridization signal, the transplanted cells also displayed strong expression of the mouse-specific neural antigen M6. Expression of this antigen is particularly pronounced in axons (Lund et al., Neurosci. Lett. 61:221-226, 1985; the M6 antibody was generously provided by C. Lagenaur, Department of Neurobiology, University of Pittsburgh School of Medicine, 818A Scaife Hall, Pittsburgh, Pa. 15261, USA, and used at a dilution of 1:10). In the recipient brains, numerous donor-derived M6-positive axons were found to project from the graft into the adjacent host brain tissue. These observations indicate that neurons derived from grafted ES cell-derived neural spheres innervate the host brain.

The invention claimed is:

1. A method for the generation of an isolated, non-tumorigenic cell composition consisting essentially of embryonic stem cell-derived neural precursor cells, and neuronal cells derived from the embryonic stem cell-derived neural precursor cells comprising:
    (a) culturing mouse or human embryonic stem cells that are not human genetically modified embryonic stem cells to produce neural precursor cells;
    (b) culturing the neural precursor cells from (a) in a first growth factor-containing serum-free medium, the first medium comprising basic fibroblast growth factor (bFGF);
    (c) culturing the cells from (b) in a second growth factor-containing serum-free medium, the second medium comprising bFGF and epidermal growth factor (EGF); and
    (d) culturing the cells from (c) in a third growth factor-containing serum-free medium, the third medium comprising bFGF and platelet-derived growth factor (PDGF), to obtain the cell composition consisting essentially of embryonic stem cell-derived neural precursor cells, and neuronal cells derived from the embryonic stem cell-derived neural precursor cells.

2. The method according to claim 1, wherein the embryonic stem cells in step (a) are in the form of cell aggregates.

3. The method according to claim 1, wherein the cells of steps (c) and (d) grow as a monolayer.

4. The method according to claim 1, comprising cells with neuronal, astroglial or oligodendroglial properties.

5. The method according to claim 1, wherein the embryonic stem cells are obtained after nuclear transfer into oocytes.

6. The method of claim 1, wherein the embryonic stem cells in (a) are cultured in serum-free medium.

7. The method of claim 2, wherein the cell aggregates are embryoid bodies.

8. A method for the generation of an isolated, non-tumorigenic cell composition comprising neural spheres, wherein the neural spheres consist essentially of embryonic stem cell-derived neural precursor cells, and neuronal cells derived from the embryonic stem cell-derived neural precursor cells comprising:
    (a) culturing mouse or human embryonic stem cells that are not human genetically modified embryonic stem cells to produce neural precursor cells;
    (b) culturing the neural precursor cells from (a) in a first growth factor containing serum-free medium, the first medium comprising bFGF;
    (c) culturing the cells from (b) in a second growth factor-containing serum-free medium, the second medium comprising bFGF and EGF to produce neural spheres consisting essentially of embryonic stem cell-derived neural precursor cells, and neuronal cells derived from the embryonic stem cellderived neural precursor cells,
    thereby producing the isolated, non-tumorigenic cell composition comprising neural spheres.

9. The method according to claim 8, wherein the embryonic stem cells in (a) are in the form of cell aggregates.

10. The method of claim 9, wherein the cell aggregates are embryoid bodies.

11. The method of claim 8, wherein the embryonic stem cells in (a) are cultured in serum-free medium.

12. The method according to claim 8, wherein the embryonic stem cells are obtained after nuclear transfer into oocytes.

13. The method according to claim 8, further comprising:
    (d) culturing the cells from step (c) in the second medium further comprising CNTF or T3 to direct differentiation of the precursor cells towards an astrocytic or an oligodendroglial fate.

14. The method according to claim 13, further comprising:
    (e) culturing the cells from step (d) in a third medium comprising ciliary neurotrophic factor (CNTF) or T3, and isolation of the precursor cells with an astrocytic or an oligodendroglial fate.

15. The method according to claim 8, wherein the procedure is combined with cell separation and cell sorting techniques.

16. The method according to claim 8, wherein the purified precursor cells are suspended in a medium suitable for injection.

* * * * *